(12) United States Patent
Baynes et al.

(10) Patent No.: US 8,192,976 B2
(45) Date of Patent: *Jun. 5, 2012

(54) BIOLOGICAL SYNTHESIS OF DIFUNCTIONAL ALKANES FROM CARBOHYDRATE FEEDSTOCKS

(75) Inventors: Brian M. Baynes, Cambridge, MA (US); John Michael Geremia, Somerville, MA (US)

(73) Assignee: Celexion, LLC, Cambridge, MA (US)

( * ) Notice: Subject to any disclaimer, the term of this patent is extended or adjusted under 35 U.S.C. 154(b) by 156 days.

This patent is subject to a terminal disclaimer.

(21) Appl. No.: 12/637,340

(22) Filed: Dec. 14, 2009

(65) Prior Publication Data

US 2010/0151536 A1 Jun. 17, 2010

Related U.S. Application Data

(60) Provisional application No. 61/201,576, filed on Dec. 12, 2008.

(51) Int. Cl.
*C12P 17/10* (2006.01)
*C12N 9/00* (2006.01)
*C12N 1/20* (2006.01)
*C12N 15/00* (2006.01)
*C07H 21/04* (2006.01)

(52) U.S. Cl. ............... 435/252.3; 435/121; 435/183; 435/320.1; 536/23.2

(58) Field of Classification Search .............. None
See application file for complete search history.

(56) References Cited

U.S. PATENT DOCUMENTS

| | | | |
|---|---|---|---|
| 3,485,821 | A | 12/1969 | Sheehan |
| 4,400,468 | A | 8/1983 | Faber |
| 4,683,195 | A | 7/1987 | Mullis |
| 4,725,542 | A | 2/1988 | Barer |
| 4,730,040 | A | 3/1988 | Vagt et al. |
| 4,929,396 | A | 5/1990 | Barer |
| 5,221,800 | A | 6/1993 | Park |
| 5,258,292 | A | 11/1993 | Yeh |
| 5,272,073 | A | 12/1993 | Frost |
| 5,487,987 | A | 1/1996 | Frost |
| 5,616,496 | A | 4/1997 | Frost |
| 5,629,190 | A | 5/1997 | Petre |
| 6,180,388 | B1 | 1/2001 | Crouzet |
| 6,365,376 | B1 | 4/2002 | Brzostowicz |
| 6,498,242 | B1 | 12/2002 | Cheng |
| 6,794,165 | B2 | 9/2004 | Cheng |
| 7,323,320 | B2 | 1/2008 | Oleinikov |
| 7,563,600 | B2 | 7/2009 | Oleinikov |
| 2002/0127666 | A1 | 9/2002 | Brzostowicz |
| 2003/0087403 | A1 | 5/2003 | Cheng |
| 2006/0160138 | A1 | 7/2006 | Church |
| 2007/0254341 | A1 | 11/2007 | Raemakers-Franken |
| 2007/0269870 | A1 | 11/2007 | Church |
| 2008/0009609 | A1 | 1/2008 | Maupin-Furlow |
| 2008/0064610 | A1 | 3/2008 | Lipovsek |
| 2008/0287320 | A1 | 11/2008 | Baynes |
| 2009/0087840 | A1 | 4/2009 | Baynes |

FOREIGN PATENT DOCUMENTS

| | | |
|---|---|---|
| WO | WO9507996 | 3/1995 |
| WO | WO03016691 | 12/2003 |
| WO | WO2008092720 | 8/2008 |
| WO | WO2008127283 | 10/2008 |
| WO | WO2009/046375 | 4/2009 |
| WO | WO2009/113853 | 9/2009 |
| WO | WO2009/113855 | 9/2009 |
| WO | WO2009/151728 | 12/2009 |

OTHER PUBLICATIONS

Andi et al. Arch Biochem Biophys. Jan. 15, 2004;421(2):243-54.*
Jia et al. Biochem J. Jun. 15, 2006;396(3):479-85.*
Lin et al. Biochemistry. Jan. 23, 2007;46(3):890-8.*
de la Plaza et al. FEMS Microbiol Lett. Sep. 15, 2004;238(2):367-74.*
Goodlove et al. Gene. Dec. 21, 1989;85(1):209-14.*
Goh et al. Mol Genet Metab. Jul. 2002;76(3):172-80.*
Miyazaki et al. Microbiology. Jul. 2004;150(Pt 7):2327-34.*
Yan et al. Yeast. Mar. 2007;24(3):189-99.*
Kingsbury et al. Eukaryot Cell. Jun. 2004;3(3):752-63.*
De Las Rivas et al. J Microbiol Biotechnol. Mar. 2007;17(3):408-13.*
Atsumi, Shota et al., "Non-fermentative pathways for synthesis of branched-chain higher alcohols as biofuels" Nature, vol. 451, pp. 86-90, 2008.
Caspi, Ron, et al., "The MetaCyc database of metabolic pathways and enzymes and the BioCyc collection of pathways/genome databases" Nucleic Acids Research, vol. 36, D623-D631, 2008.
Fotheringham Ian, "Engineering biosynthetic pathways: new routes for chiral amino acids" Current opinion in Biology, vol. 4, pp. 120-124, 2000.
Jones Prather, Kristala L., et al., "*De novo* biosynthetic pathways: rational design of microbial chemical factories" Current Opinion in Biotechnology, vol. 19, pp. 468-474, 2008.
Niu, Wei et al., "Benzene-free synthesis of adipic acid" Biotechnol. Prog., vol. 18, pp. 201-211, 2002.
The International Search Report mailed Aug. 10, 2010.
de la Plaza M. et al. "Biochemical and molecular characterization of α-ketoisovalerate decarboxylase, an enzyme involved in the formation of aldehydes from amino acids by *Lactococcus lactis*" FEMS Microbiology Letters 238, pp. 367-374, 2004.
De Las Rivas B. et al. "Gene cloning, expression, and functional characterization of an ornithine decarboxylase protein from *Serratia liquefaciens* IF165" J. Microbial. Biotechnol., 17(3), pp. 408-413, 2007.
Goh D.L. M. et al. "Characterization of the human gene encoding α-aminoadipate aminotransferase (AADAT)" Molecular Genetics and Metabolism, 76, pp. 172-180, 2002.

(Continued)

*Primary Examiner* — Christian Fronda
(74) *Attorney, Agent, or Firm* — Jennifer A. Camacho; Natalie Salem; Greenberg Traurig, LLP

(57) ABSTRACT

Aspects of the invention relate to methods for the production of difunctional alkanes in host cells. In particular, aspects of the invention describe components of genes associated with the difunctional alkane production from carbohydrate feedstocks in host cells. More specifically, aspects of the invention describe metabolic pathways for the production of adipic acid, aminocaproic acid, caprolactam, and hexamethylenediamine via 2-ketopimelic acid.

17 Claims, 6 Drawing Sheets

OTHER PUBLICATIONS

Kingsbury J.M. et al. "Novel chimeric spermidine synthase-saccharopine dehydrogenase gene (SPE3-LYS9) in the human pathogen *Cryptococcus neoformans*" Eukaryotic Cell, 3(3), pp. 752-763, 2004.

Miyazaki T. et al. "α-Aminoadipate aminotransferase from an extremely thermophilic bacterium, *Thermus thermophilus*" Microbiology, 150, pp. 2327-2334, 2004.

Yan H. et al. "Cloning, sequencing and characterization of the α-aminoadipate reductase gene (LYS2) from *Saccharomycopsis fibuligera*" Yeast, 24, pp. 189-199, 2007.

Zhang et al., "Expanding metabolism for synthesis of nonnatural alchols" P.N.A.S, 2008, vol. 105, No. 52, pp. 20653-20658.

Howell et al., "Alpha-keto acid chain elongation reactions involved in the biosynthesis of coenzyme B (7-mercaptoheptanoyl threonine phosphate) in methanogenic Archaea", Biochemistry, 1998, vol. 37, No. 28, pp. 1010810117.

Zheng. et al. "Purification of the Azotobacter vinelandii nifV-encoded homocitrate synthase". J. Bacteril., 1997, vol. 179, No. 18, pp. 5963-5966.

Goodlove et al., "Cloning and sequence analysis of the fermentative alcohol-dehydrogenase-encoding gene of *Escherichia coli*.", Gene, 1989, vol. 85, No. 1, pp. 209-214.

Howell et al., "Identification of Enzymes Homologous to Isocitrate Dehydrogenase That Are Involved in Coenzyme B and Leucine Biosynthesis in Methanoarchaea", J. Bacteriol., 2000, vol. 182, No. 17, pp. 5013-5016.

Drevland et al., "Methanogen Homoaconitase Catalyzes Both Hydrolyase Reactions in Coenzyme B Biosynthesis", Journal of Biological Chemistry, vol. 283, pp. 28888-28896, (2008).

Tanaka et al., "Metabolism of cyclohexanol by *Pseudomonas* sp." Hakko Kagaku Kaishi (1977), 55(2), 62-7.

Donoghue and Trudgill "The metabolism of cyclohexanol by Acinetobacter NCIB 9871." Eur J Biochem. 1975, vol. 60, No. 1, pp. 1-7.

Iwaki et al. "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them" Applied and Environmental Microbiology, 1999, p. 5158-5162, vol. 65, No. 11.

* cited by examiner

BIOLOGICAL SYNTHESIS OF DIFUNCTIONAL ALKANES FROM CARBOHYDRATE FEEDSTOCKS

RELATED APPLICATIONS

This application claims the benefit of U.S. Provisional Application No. 61/201,576, filed Dec. 12, 2008, which application is hereby incorporated by reference in its entirety.

FIELD OF INVENTION

Aspects of the invention relate to methods for the production of difunctional alkanes in host cells. In particular, aspects of the invention describe components of gene associated with the difunctional alkane production from carbohydrates feedstocks in host cells. More specifically, aspects of the invention describe metabolic pathways for the production of adipic acid, aminocaproic acid, caprolactam, hexamethylenediamine via 2-ketopimelic acid.

BACKGROUND

Crude oil is the number one starting material for the synthesis of key chemicals and polymers. As oil becomes increasingly scarce and expensive, biological processing of renewable raw materials in the production of chemicals using live microorganisms or their purified enzymes becomes increasingly interesting. Biological processing, in particular, fermentations have been used for centuries to make beverages. Over the last 50 years, microorganisms have been used commercially to make compounds such as antibiotics, vitamins, and amino acids. However, the use or microorganisms for making industrial chemicals has been much less widespread. It has been realized only recently that microorganisms may be able to provide an economical route to certain compounds that are difficult or costly to make by conventional chemical means.

SUMMARY OF THE INVENTION

Aspects of the invention relate to a metabolically engineered host cell for the production α,ω difunctional Cn alkane from α-ketoacid wherein α and ω terminal functional groups are selected from the group of —OH, —COOH and —NH3 and wherein n is an integer in the range of 4 to 8, the metabolically engineered host cell being genetically modified with a nucleic acid comprising at least one nucleotide sequence encoding at least one biosynthetic pathway enzyme In some embodiments, the nucleic acid comprises nucleotide sequences encoding two or more gene products. The metabolically engineered host cell can be a prokaryotic cell. For example, in some embodiments, the metabolically engineered host cell is an anaerobic prokaryotic cell. The metabolically engineered host cell may be selected from the group consisting of *E. Coli, C. glutanicum, B. flavum* and *B. lactofermentum*.

In preferred embodiments, α-ketoacid is α-ketoglutarate and is converted to α-ketoadipate, α-ketopimelate or α-ketosuberate. In preferred embodiments, the host cell comprises nucleic acid sequences encoding a homocitrate synthase, a homoaconitase and a homoisocitrate dehydrogenase. The homocitrate synthase may be selected form the group consisting of AksA, NifV, hcs and Lys20/21. The homoaconitase may be selected form the group consisting of AksD/E, LysT/U, Lys4,3-isopropylmalate dehydratase large/small subunits, and homologs thereof. The homoisocitrate dehydrogenase may be selected from the group consisting of AksF, Hicdh, Lys12, 2-oxosuberate synthase, 3-isopropylmalate dehydrogenase and homologs thereof.

In preferred embodiments, the α,ω difunctional alkane has six carbon atoms and is selected from the group consisting of amino caproic acid, adipate, hexamethylenediamine, 6 hydroxyhexamine, 1,6-hexane diol, 6-aminohexanal, 6-aminohexanol and 6-hydroxyhexanoate.

Aspects of the invention relates to a metabolically engineered host cells for the production of adipic acid from α-ketopimelate, the host cell further comprising a nucleic acid encoding a decarboxylase enzyme and an aldehyde dehydrogenase enzyme. In some embodiments, the decarboxylase enzyme is a 2-keto decarboxylase and catalyzes the conversion of α-ketopimelate to adipate semialdehyde and the aldehyde dehydrogenase catalyzes the conversion of adipate semialdehyde to adipic acid. The 2-ketodecarboxylase may be selected from the group of 2-ketoglutarate decarboxylase (kgd), 2-ketoisovalerate decarboxylase (kivD), transaminated amino acid decarboxylase (ARO10), benzoylformate decarboxylase (mdlC), 2-ketoarginine decarboxylase (aruI), phosphonopyruvate decarboxylase (fom2), pyruvate decarboxylase isozyme (PDC6, PDC1), pyruvate decarboxylase isozyme 2 (PDC5, PDC1, PDC6, Aro10, KivD), indolpyruvate decarboxylase (ipdC) and homologs thereof. In some embodiments, the decarboxylase has at least 30% identity when compared to 2-ketoglutarate decarboxylase (kgd), 2-ketoisovalerate decarboxylase (kivD), transaminated amino acid decarboxylase (ARO10), benzoylformate decarboxylase (mdlC), 2-ketoarginine decarboxylase (aruI), phosphonopyruvate decarboxylase (fom2), pyruvate decarboxylase isozyme (PDC6, PDC1), pyruvate decarboxylase isozyme 2 (PDC5, PDC1, PDC6, Aro10, KivD), indolpyruvate decarboxylase (ipdC) and homolgs thereof. In preferred embodiments, the aldehyde dehydrogenase is a 6-oxohexanoate dehydrogenase (ChnE) and homologs thereof. In other embodiments, the aldehyde dehydrogenase has at least 30% identity to the 6-oxohexanoate dehydrogenase (ChnE).

Aspects of the invention relates to metabolically an engineered host cell for the production of amino caproic acid from α-ketopimelate, the host cell further comprising a nucleic acid encoding an aminotransferase enzyme and a decarboxylase. In some embodiments, the 2-aminotransferase catalyzes the conversion of α-ketopimelate to 2-aminopimelate and the decarboxylase catalyzes the conversion of 2-aminopimelate to amino caproic acid. The aminotransferase may be selected form the group consisting of α-aminoadipate aminotransferase-1 (AADAT), aminoadipate aminotransferase (LysN), diaminopimelate dehydrogenase (ddb and dapdh) and homologs thereof. In some embodiments, the decarboxylase is a glutamate decarboxylase. In some embodiments, the glutamate decarboxylase is encoded by a gene or fragment of a gene selected from the group consisting of Gad6/7, GadA, GadB and lysA. In some embodiments, the decarboxylase catalyzes the conversion of α-ketopimelate to adipate semialdehyde and the aminotransferase catalyzes the conversion of adipate semialdehyde to amino caproic acid. The ketodecarboxylase may be selected from the group of 2-ketoglutarate decarboxylase (kgd), 2-ketoisovalerate decarboxylase (kivD), transaminated amino acid decarboxylase (ARO10), benzoylformate decarboxylase (mdlC), 2-ketoarginine decarboxylase (aruI), phosphonopyruvate decarboxylase (fom2), pyruvate decarboxylase isozyme (PDC6, PDC1), pyruvate decarboxylase isozyme 2 (PDC5, PDC1, PDC6, Aro10, KivD), indolpyruvate decarboxylase (ipdC) and homologs thereof. The aminotransferase may be selected form the group consisting of GABA transaminase, Lys6 dehydrogenase, ornithine-oxo acid transaminase, lysine aminotransferase, 4-aminobutyrate aminotransferase, 4-aminobutyrate aminotransferase, 4-aminobutyrate aminotransferase, Saccharopine dehydrogenase (LYS9 and LYS1) or any homologous proteins thereof.

Aspects of the invention relate to the production of hexamethylenediamine from amino caproic acid, the host cell comprising a nucleic acid encoding an aldehyde dehydrogenase and an amino-transferase. In some embodiments, the aldehyde dehydrogenase catalyzes the conversion of aminocaproic acid to 6-aminohexanal and the aminotransferase catalyzes the conversion of 6-aminohexanal to 6-hexamethylenediamine. In preferred embodiments, the aldehyde dehydrogenase is an ALDH enzyme (EC 1.2.1-). In some embodiments, the aminotransferase may be selected form the group consisting of α-aminoadipate aminotransferase-1 (AADAT), aminoadipate aminotransferase (LysN), diaminopimelate dehydrogenase (ddb, dapdh) and homologous proteins thereof.

Aspects of the invention relates to a metabolically engineered host cell for the production of hexamethylenediamine from α-ketopimelate, the host cell comprising a nucleic acid encoding an aminotransferase, a reductase, a dehydrogenase and a decarboxylase. In some embodiments, the aminotransferase catalyzes the conversion of α-ketopimelate to 2 aminopimelate, the reductase catalyzes the conversion of 2-aminopimelate to 2-amino-7-oxoheptanoate, the dehydrogenase catalyzes the conversion of 2-amino-7-oxoheptanoate to 2,7-diaminoheptanoate, and the decarboxylase catalyzes the conversion of 2,7-diaminoheptanoate to hexamathylenediamine. The aminotransferase may be selected from the group consisting of α-aminoadipate aminotransferase-1 (AADAT), aminoadipate aminotransferase (LysN), diaminopimelate dehydrogenase (ddb, dapdh) and variants thereof. In some embodiments, the reductase is an amino adipate reductase or homolog thereof. In some embodiments, the amino adipate reductase is encoded by Sc-Lys2. In some embodiments, the dehydrogenase is a saccharopine dehydrogenase or homolog thereof and is encoded by Sc-Lys9 or Sc-Lys1 or variants thereof. The decarboxylase may be selected from the group consisting of lysine decarboxylase, ornithine decarboxylase and variants thereof.

Some aspects of the invention relate to a metabolically engineered host cell for the production of 6-hydroxyhexanoate from α-ketopimelate, the host cell comprising a nucleic acid encoding an alcohol dehydrogenase. Other aspects of the invention relate to a metabolically engineered host cell for the production of 1,6-hexanediol from 6-hydroxyhexanoate, the host cell comprising a nucleic acid encoding an alcohol dehydrogenase or aldehyde dehydrogenase. The alcohol dehydrogenase may be selected from a 6-hydroxyhexanoate dehydrogenase, a butanol dehydrogenase, a ADHIV dehydrogenase, a propanediol oxidoreductase, an ADH6 and homologs thereof.

Aspects of the invention relate to methods of producing a α,ω difunctional Cn alkane from α-ketoglutarate wherein α and ω terminal functional groups are selected from the group of —OH, —COOH and —NH3 and wherein n is an integer in the range of 4 to 7 comprising culturing the host cell under conditions sufficient to produce a α,ω difunctional Cn alkane; and separating the α,ω difunctional Cn alkane.

In some aspects, the invention relates to a host cell comprises one or more exogenous nucleic acid sequence encoding at least one polypeptide selected from homocitrate synthase (EC 2.3.3.-), homoaconitase (EC 2.3.3.14), homoisocitrate dehydrogenase (EC 1.1.1.-) and combination thereof. In some embodiments, the metabolic engineered host cells produce α-ketoadipate, α-ketopimelate, α-ketosuberate or a combination thereof from α-ketoglutarate. In some embodiments, the engineered host cell comprises one or more exogenous nucleic acid sequence encoding at least one polypeptide selected from α-ketoacid decarboxylase (EC 4.1.1.-) and a dehydrogenase (EC 1.1.1.-) and combination thereof. In some embodiments, the engineered host cell produces a Cn dicarboxylic acid wherein n is an integer of the range of 4 to 7. For example, the engineered host cell produces adipate. In other embodiments, the engineered host cell produce a Cn hydroxycarboxylic acid wherein n is an integer of the range of 4 to 7. For example, the engineered host cells produce 6-hydroxyhexanoate. Yet in other embodiments, the engineered host cell produces a Cn alkane diol wherein n is an integer of the range of 4 to 7, for example, 1,6-hexanediol.

In some aspects of the invention, the engineered host cell producing α-ketoadipate, α-ketopimelate, α-ketosuberate or a combination thereof from α-ketoglutarate, comprises one or more exogenous nucleic acid sequence encoding at least one polypeptide selected from α-ketoacid decarboxylase (EC 4.1.1.-), an amino transferase (EC 1.4.1.-), an amino transferase (EC 2.6.1.-) and combination thereof. In preferred embodiments, the engineered host cell produces amino caproic acid. In some embodiments, the engineered host cell comprises furthermore, one or more exogenous nucleic acid sequence encoding at least one polypeptide selected from aldehyde dehydrogenase (EC 1.2.1.3) and produces a Cn amino aldehyde or a Cn diamino alkane wherein n is an integer of the range of 4 to 7. For example, the engineered host cell produces hexamethylenediamine or 6-hydroxyhexamine In some embodiments, the engineered host cell comprises one or more exogenous nucleic acid sequence encoding at least one polypeptide selected from an aminoadipate transferase (EC 2.6.1.39), a diaminopimelate dehydrogenase (EC 1.4.1.16), a glutamate decarboxylase (EC 4.1.1.-) and combination thereof. In some embodiments, the host cell produces a Cn amino-carboxylic acid wherein n is an integer of the range of 4 to 7. For example, the engineered host cell of claim produces amino caproic acid.

Some aspects of the invention relate to an engineered host cell for the production of α,ω difunctional Cn alkanes from α-ketoacid comprising one or more exogenous nucleic acid sequence encoding at least one polypeptide selected from α-aminoadipate-aminotransferase (EC 2.6.1.39), diaminopimelate dehydrogenase (EC1.4.1.16), an amino adipate reductase (EC 1.2.1.31), a saccharopine dehydrogenase (EC 1.5.1.-), a lysine decarboxylase (EC 4.1.1.18), an ornithine decarboxylase (EC4.1.1.17) and combination thereof. In some embodiments, the engineered host cell produces a Cn amino aldehyde or a Cn diamino alkane wherein n is an integer of the range of 4 to 7. For example, the engineered host cell produces hexamethylenediamine. In some aspects of the invention, the engineered host cell further comprises one or more exogenous nucleic acid sequence encoding at least one polypeptide selected from an 3-oxoacyl-[acyl-carrier-protein] reductase (EC 1.1.1.100), a fatty acid synthase (EC 2.3.1.-), a dehydratase (EC 4.2.1.59), 3-hydroxyoctanoyl-[acyl-carrier-protein] dehydratase (EC 4.2.1.59), an enoyl-[acyl-carrier-protein] reductase (EC 1.3.1.9) and combination thereof. In some preferred embodiments, the engineered host cell produces a Cn dicarboxylic acid wherein n is an integer of the range of 5 to 8. For example, the engineered host cell produces adipate. In some embodiments, the engineered host cell further comprises one or more exogenous nucleic acid sequence encoding at least one polypeptide selected from an aldehyde dehydrogenase (EC 1.2.1.3) and produces a Cn hydroxycarboxylic acid wherein n is an integer of the range of 5 to 8, for example 6-hydroxyhexanoate. In some embodiments, the engineered host cell produces a Cn alkane diol wherein n is an integer of the range of 5 to 8, for example 1,6-hexanediol.

Some aspects of the invention relate to an engineered host cell for the production of α,ω difunctional Cn alkanes from α-ketoacid comprising one or more exogenous nucleic acid sequence encoding at least one polypeptide selected from α-aminoadipate-aminotransferase (EC 2.6.1.39), diaminopimelate dehydrogenase (EC1.4.1.16), an amino adipate reductase (EC 1.2.1.31), a saccharopine dehydrogenase (EC 1.5.1.-), a lysine decarboxylase (EC 4.1.1.18), an ornithine decarboxylase (EC4.1.1.17) and combination thereof, selected from an 3-oxoacyl-[acyl-carrier-protein] reductase (EC 1.1.1.100), a fatty acid synthase (EC 2.3.1.-), a dehydratase (EC 4.2.1.59), 3-hydroxyoctanoyl-[acyl-carrier-protein] dehydratase (EC 4.2.1.59), an enoyl-[acyl-carrier-protein] reductase (EC 1.3.1.9) and combination thereof, at least one polypeptide selected from an aldehyde dehydrogenase, and one or more exogenous nucleic acid sequence encoding at least one polypeptide selected from an amino transferase (EC 1.4.1.-) and an amino transferase (EC 2.6.1.-). In some embodiments, the host cell produces a Cn amino carboxylic acid wherein n is an integer of the range of 5 to 8, for example amino caproic acid. In some embodiments, the engineered host cell further comprises one or more exogenous nucleic acid sequence encoding at least one polypeptide selected from aldehyde dehydrogenase (EC 1.2.1.3), amino transferase (EC 1.4.1.-) and an amino transferase (EC 2.6.1.-) and combination thereof. In some embodiments, the engineered host cell produces a 1,n-diaminoalkane wherein n is an integer of the range of 5 to 8, for example hexamethylenediamine. In other embodiments, the engineered host cell produces an n-amino alcohol wherein n is an integer of the range of 5 to 8, for example 6-aminohexanol.

Some aspects of the invention, relates to an engineered host cell comprising one or more exogenous nucleic acid sequence encoding at least one polypeptide selected from aminotransferase (EC 2.6.1.7), an aldehyde dehydrogenase (EC 1.2.1.3), a glutamate semialdehyde mutase (EC 5.4.3.8), 3-oxoacyl-[acyl-carrier-protein] reductase (EC 1.1.1.100), a fatty acid synthase (EC 2.3.1.-), a dehydratase (EC 4.2.1.59), 3-hydroxyoctanoyl-[acyl-carrier-protein] dehydratase (EC 4.2.1.59), an enoyl-[acyl-carrier-protein] reductase (EC 1.3.1.9) and combination thereof. In some embodiments, the engineered host cell produces a n-amino carboxylic acid wherein n is an integer of the range of 5 to 8, for example amino caproic acid.

Some aspects of the invention relate to a method of producing a α,ω difunctional Cn alkane from α-ketoglutarate wherein α and ω terminal functional groups are selected from the group of —OH, —COOH and —NH3 and wherein n is an integer in the range of 5 to 8, the method comprising culturing the engineered host cell under conditions sufficient to produce a α,ω difunctional Cn alkane; and separating the α,ω difunctional Cn alkane.

BRIEF DESCRIPTION OF THE DRAWINGS

The invention can be more fully understood from the following detailed description and the figures which form part of the application.

DETAILED DESCRIPTION OF THE INVENTION

Figure 1A:
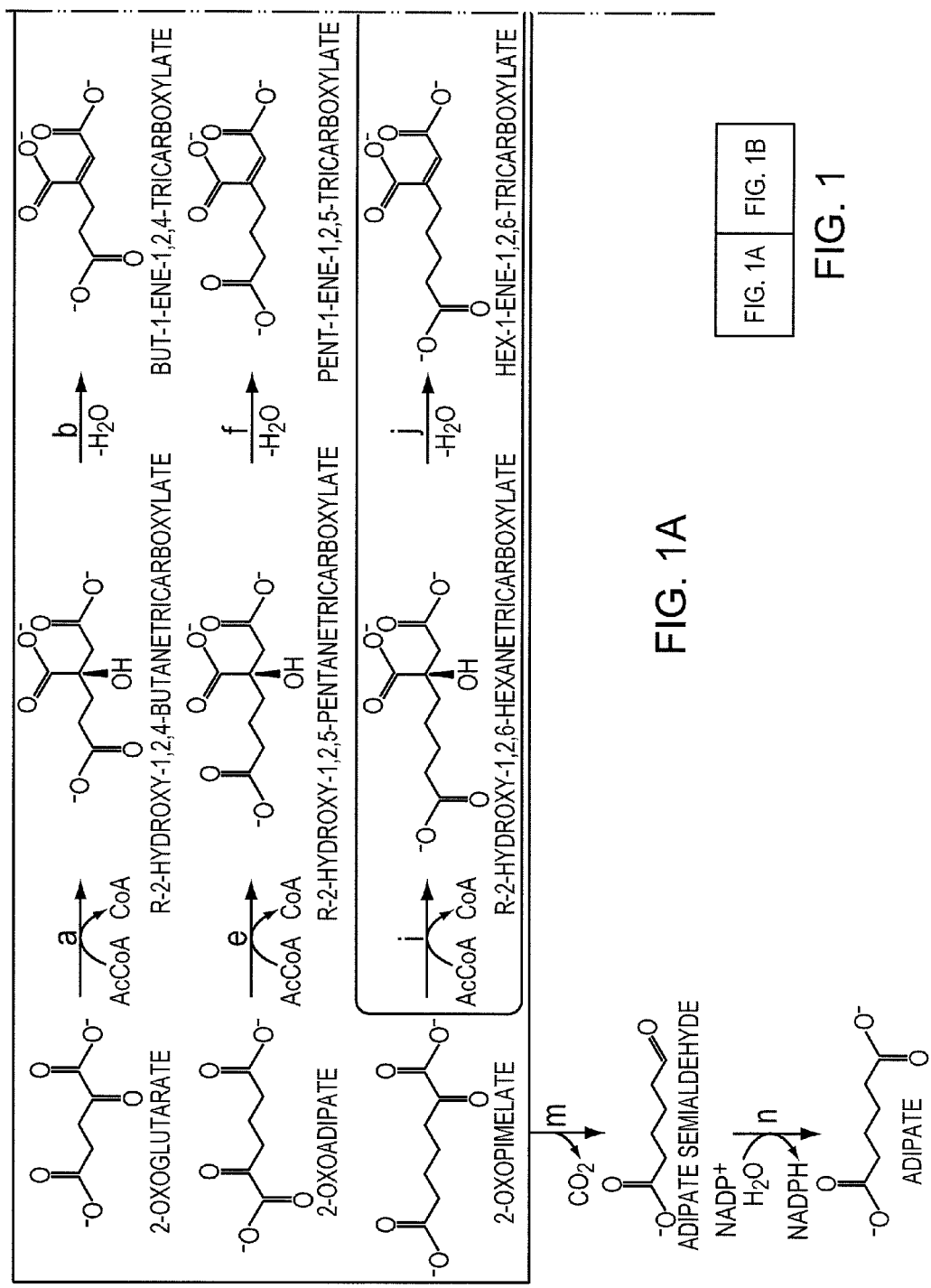
FIG. 1 shows an adipic acid biosynthetic pathway. The steps a through l describes the 2-keto elongation pathway from the Coenzyme B biosynthesis pathway from *Methanococcus jannaschii*. Labeled steps a, b, c, d, e, f, g, h, m, and n represent the substrate to product conversion described below.

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The terms "comprise" and "comprising" are used in the inclusive, open sense, meaning that additional elements may be included.

The term "including" is used to mean "including but not limited to". "Including" and "including but not limited to" are used interchangeably.

All publications mentioned herein are incorporated herein by reference. The publications discussed herein are provided solely for their disclosure prior to the filing date of the present invention. Nothing herein is to be construed as an admission that the present invention is not entitled to antedate such publication by virtue of prior invention.

Aspects of the invention provide methods and materials for producing organic aliphatic compounds of interest in a rapid, inexpensive and environmentally responsible way. As such, the present invention meets a number of commercial and industrial needs. The term "organic molecule" refers, for example, to any molecule that is made up predominantly of carbon and hydrogen, such as, for example, alkanes. Organic compounds of interest, such as difunctional alkanes, diols, dicarboxylic acids, etc. can be used to synthesize plastic, nylons and other products usually derived from petroleum and hydrocarbons. Aspects of the invention relate to the synthesis of difunctional n-alkanes which hydrocarbon chains $C_n$ is derived from a hydrocarbon chain $C_n$ or $C_{n+1}$ in which n is a number of from about 1 to about 8, such as from about 2 to about 5 or from about 3 to about 4. In a preferred embodiment, the difunctional n-alkanes are derived from an α-(n+1) or n keto acid.

Aspects of the invention relate to the production of difunctional alkanes of interest in a microorganism and provide methods for the production of difunctional alkanes from a carbohydrate source in a microorganism. As used herein "difunctional alkanes" refers alkanes having two functional groups. The term "functional group" refers, for example, to a group of atoms arranged in a way that determines the chemical properties of the group and the molecule to which it is attached. Examples of functional groups include halogen atoms, hydroxyl groups (—OH), carboxylic acid groups (—COOH) and amine groups (—NH2) and the like. "Alcohol" refers, for example, to an alkyl moiety in which one or more of the hydrogen atoms has been replaced by an —OH group. The term "primary alcohol" refers, for example, to alcohols in which the —OH group is bonded to a terminal or chain-ending carbon atom, such as in 1-butanol, 1-hexanol and the like. The term "secondary alcohol" refers, for example to alcohols in which the —OH group is bonded to a carbon atom that is bonded to one hydrogen atom and to two other carbon atoms, such as in 2-butanol, 2-hexanol and the like. The term "tertiary alcohol" refers, for example to alcohols in which the —OH group is bonded to a carbon atom that is bonded to three other carbon atoms, such as in methylpropanol (tert-butanol) and the like. "Amine" refers, for example, to an alkyl moiety in which one or more of the hydrogen atoms has been replaced by an —NH$_2$ group. "Carbonyl compound" refers, for example, to an organic compound containing a carbonyl group, C=O, such as, for example, aldehydes, which have the general formula RCOH; ketones, which have the general formula RCOR; carboxylic acids, which have the general formula RCOOH; and esters, which have the general formula RCOOR'.

The method incorporates microorganisms capable of producing one of the following difunctional alkanes of interest, particularly, adipic acid, amino caproic acid, HMD, 6-hydroxyhexanoate. Other difunctional alkanes of interest include 1,3-propanediol, glycerol, acrylic acid, cadaverin, 3-hydroxypropionic acid, pentamethylenediamine, maleic acid, succinic acid, adipic acid, sebacic acid, glutaric acid, and suberic acid etc. Several chemical synthesis routes have been described, for example, for adipic acid and its intermediates such as muconic acid and adipate semialdehyde; for caprolactam, and its intermediates such as 6-amino caproic acid; for hexane 1,6 diamino hexane or hexanemethylenediamine; for 3-hydroxypropionic acid and its intermediates such as malonate semialdehyde, but only a few biological routes have been disclosed for some of these organic chemicals. Therefore, aspects of the invention provide engineered metabolic routes, isolated nucleic acids or engineered nucleic acids, polypeptides or engineered polypeptides, host cells or genetically engineered host cells, methods and materials to produce difunctional alkanes from sustainable feedstock. Carbon sources suitable for starting point include carbohydrates and synthetic intermediates. Examples of carbohydrates which cell are capable of metabolizing include sugars, dextroses, triglycerides and fatty acids. Intermediates products from metabolic pathway such as pyruvate, oxaloacetate, 2-ketoglutatrate can also be used as starting points. Aspects of the invention relates to engineered polypeptides and polynucleotides encoding the enzymes having an activity or an improved activity on a natural or an unnatural substrate or having broad substrate specificity (e.g. catalytic promiscuity such as substrate promiscuity). The term "polypeptide" and the terms "protein" and peptide" which are used interchangeably herein, refers to a polymer of amino acids, including, for example, gene products, naturally-occurring proteins, homologs, orthologs, paralogs, fragments, and other equivalents, variants and analogs of the forgoing. The term "polypeptide having enzymatic activity" refers to any polypeptide that catalyzes a chemical reaction of other substances without itself being destroyed or altered upon completion of the reaction. Typically, a polypeptide having enzymatic activity catalyzes the formation of one or more products from one or more substrates. In some aspects of the invention, the catalytic promiscuity properties of some enzymes may be combined with protein engineering and may be exploited in novel metabolic pathways and biosynthesis applications. In some embodiments, existing enzymes are modified for use in organic biosynthesis. In some preferred embodiments, the enzymes involved in the production of the difunctional n-alkanes of interest include but are not limited to 2 amino-decarboxylases, 2-ketodecarboxylases, terminal-aminotransferases, 2-aminotransferases, alcohol dehydrogenases, aldehyde dehydrogenases, amino-aldehyde dehydrogenases, dehydrogenases and dehydratases. In some embodiments, the reaction mechanism of the enzyme may be altered to catalyze new reactions, to change, expand or improve substrate specificity. One should appreciate that if the enzyme structure (e.g. crystal structure) is known, enzymes properties may be modified by rational redesign (see US patent application US20060160138, US20080064610 and US20080287320 which are incorporated by reference in their entirety). Modification or improvement in enzyme properties may arise from introduction of modifications into a polypeptide chain that may, in effect, perturbs the structure-function of the enzyme and/or interaction with another molecule (e.g., substrate versus unnatural substrate). It is well known in the art that some regions of the polypeptide may be critical to enzyme activity. For example, small perturbation in composition of amino acids involved in catalysis and/or in substrate binding domains will have significant effects on enzyme function. Some amino acid residues may be at important positions for maintaining the secondary or tertiary structure of the enzyme, and thus also produce noticeable changes in enzyme properties when modified. In some embodiments, the potential pathway components are variants of any of the foregoing. Such variants may be produced by random mutagenesis or may be produced by rational design for production of an enzymatic activity having, for example, an altered substrate specificity, increased enzymatic activity, greater stability, etc. Thus, in some embodiments, the number of modifications to a reference parent enzyme that produces an enzyme having the desired property may comprise one or more amino acids, 2 or more amino acids, 5 or more amino acids, 10 or more amino acids, or 20 or more amino acids, up to 10% of the total number of amino acids, up to 20% of the total number of amino acids, up to 30% of the total number of amino acids, up to 40% of the total number of amino acids making up the reference enzyme or up to 50% of the total number of amino acids making up the reference enzyme.

Those skilled in the art will understand that engineered pathways exemplified herein are described in relation to, but are not limited to, species specific genes and encompass homologs or orthologs of nucleic acid or amino acid sequences. Homologs and orthologs sequences possess a relatively high degree of sequence identity/similarity when aligned using methods known in the art.

Aspects of the invention relates to new microorganisms or "genetically modified" microorganisms or host cells that have been engineered to possess new metabolic capabilities or new metabolic pathways. As used herein the term "genetically modified" microorganisms refers to microorganisms having at least one genetic alteration not normally found in the wild type strain of the references species. In some embodiments, genetically engineered microorganisms are engineered to express or overexpress at least one particular enzyme at critical points in a metabolic pathway, and/or block the synthesis of other enzymes, to overcome or circumvent metabolic bottlenecks. The term "metabolic pathway" refers to a series of two or more enzymatic reactions in which the product of one enzymatic reaction becomes the substrate for the next enzymatic reaction. At each step of a metabolic pathway, intermediate compounds are formed and utilized as substrates for a subsequent step. These compounds may be called "metabolic intermediates." The products of each step are also called "metabolites."

Aspects of the invention provide methods for designing and making engineered metabolic pathways. In some aspects of the invention, alternative pathways for making a product of interest from one or more available and sustainable substrates may be made in one or more host cell or microorganisms of interest. One should appreciate that the engineered pathway for making the difunctional alkanes of interest may involve multiple enzymes and therefore the flux through the pathway may not be optimum for the production of the product of interest. Consequently, in some aspects of the invention flux is optimally balanced by modulating the activity level of the pathway enzymes relative to one another. Examples of such modulation are provided throughout the application.

Aspects of the invention provide genetically modified host cells or microorganism and methods of using the same to produce difunctional n-alkanes from α-keto acids. A host cell as used herein refers to an in vivo or in vitro eukaryotic cell, a prokaryotic cell or a cell from a multicellular organism (e.g. cell line) cultured as a unicellular entity. A host cell may be prokaryotic (e.g., bacterial such as *E. coli* or *B. subtilis*) or eukaryotic (e.g., a yeast, mammal or insect cell). For example, host cells may be bacterial cells (e.g., *Escherichia coli, Bacillus subtilis, Mycobacterium* spp., *M. tuberculosis*, or other suitable bacterial cells), Archaea (for example, *Methanococcus Jannaschii* or *Methanococcus Maripaludis* or other suitable archaic cells), yeast cells (for example, *Saccharomyces* species such as *S. cerevisiae, S. pombe, Picchia* species, *Candida* species such as *C. albicans*, or other suitable yeast species). Eukaryotic or prokaryotic host cells can be, or have been, genetically modified (also referred as "recombinant host cell", "metabolic engineered cells" or "genetically engineered cells") and are used as recipients for a nucleic acid, for example, an expression vector that comprises a nucleotide sequence encoding one or more biosynthetic or engineered pathway gene products. Eukaryotic and prokaryotic host cells also denote the progeny of the original cell which has been genetically engineered by the nucleic acid. In some embodiments, a host cell may be selected for its metabolic properties. For example, if a selection or screen is related to a particular metabolic pathway, it may be helpful to use a host cell that has a related pathway. Such a host cell may have certain physiological adaptations that allow it to process or import or export one or more intermediates or products of the pathway. However, in other embodiments, a host cell that expresses no enzymes associated with a particular pathway of interest may be selected in order to be able to identify all of the components required for that pathway using appropriate sets of genetic elements and not relying on the host cell to provide one or more missing steps.

In some embodiments, anaerobic bacterial organisms are metabolically engineered. As used herein, an anaerobic organism is any organism that does not require oxygen for growth (i.e. anaerobic conditions) Advantageously, the bacterial cell can be an *E. coli, C. glutamicum, B. flavum* or *B. lactofermentum* cell; these strains are currently being employed industrially to make amino compounds using bacterial fermentation processes. For example, *C. glutanicum* has been used extensively for amino acid production (e.g. L-glutamate, L-Lysine, see Eggleging L et al., 2005, Handbook for *Corynebacterium glutanicum*. Boca Raton, USA: CRC Press).

The metabolically engineered cell of the invention is made by transforming a host cell with at least one nucleotide sequence encoding enzymes involved in the engineered metabolic pathways. As used herein the term "nucleotide sequence", "nucleic acid sequence" and "genetic construct" are used interchangeably and mean a polymer of RNA or DNA, single- or double-stranded, optionally containing synthetic, non-natural or altered nucleotide bases. A nucleotide sequence may comprise one or more segments of cDNA, genomic DNA, synthetic DNA, or RNA. In a preferred embodiment, the nucleotide sequence is codon-optimized to reflect the typical codon usage of the host cell without altering the polypeptide encoded by the nucleotide sequence. In certain embodiments, the term "codon optimization" or "codon-optimized" refers to modifying the codon content of a nucleic acid sequence without modifying the sequence of the polypeptide encoded by the nucleic acid to enhance expression in a particular host cell. In certain embodiments, the term is meant to encompass modifying the codon content of a nucleic acid sequence as a mean to control the level of expression of a polypeptide (e.g. either increase or decrease the level of expression). Accordingly, aspects of the invention include nucleic sequences encoding the enzymes involved in the engineered metabolic pathways. In some embodiments, a metabolically engineered cell may express one or more polypeptide having an enzymatic activity necessary to perform the steps described below. For example a particular cell may comprises one, two, three, four, five or more than five nucleic acid sequences, each one encoding the polypeptide(s) necessary to perform the conversion of α-ketoacid into difunctional alkane. Alternatively, a single nucleic acid molecule can encode one, or more than one, polypeptide. For example, a single nucleic acid molecule can contain nucleic acid sequences that encode two, three, four or even five different polypeptides. Nucleic acid sequences useful for the invention described herein may be obtained from a variety of sources such as, for example, amplification of cDNA sequences, DNA libraries, de novo synthesis, excision of genomic segment. The sequences obtained from such sources may then be modified using standard molecular biology and/or recombinant DNA technology to produce nucleic sequences having desired modifications. Exemplary methods for modification of nucleic acid sequences include, for example, site directed mutagenesis, PCR mutagenesis, deletion, insertion, substitution, swapping portions of the sequence using restriction enzymes, optionally in combination with ligation, homologous recombination, site specific recombination or various combination thereof. In other embodiments, the nucleic acid sequences may be a synthetic nucleic acid sequence. Synthetic polynucleotide sequences may be produce using a variety of methods described in U.S. Pat. No. 7,323,320, in copending application having Ser. No. 11/804,996, and in U.S. Patent Publication Nos. 1006/0160138 and 2007/0269870, which are incorporated herein by reference in their entirety.

Methods of transformation for bacteria, plant, and animal cells are well known in the art. Common bacterial transformation methods include electroporation and chemical modification.

In some embodiments, a genetically modified host cell is genetically modified such that it produces, when cultured in vitro in a suitable medium, the product of interest or an intermediate at a level of at least 0.1 g/l, at least 1 g/l or at least 10 g/l. One should appreciate that the level of the product of interest or its metabolic intermediates produced by a genetically modified host cell can be controlled in various ways. In some embodiments, the level of expression is controlled by the number of copy of the nucleic acid sequences encoding one or more enzymes involved in the engineered pathway (e.g. high copy expression vector versus medium or low copy expression vectors). Preferably, the nucleic acid sequences are introduced into the cell using a vector. Low copy expression vectors generally provide fewer than 20 vectors copies per cell (e.g. from 1 to about 5, from 5 to about 10, from 10 to about 15, from 15 to about 20 copies expression vector per cell. Suitable low copy expression vectors for prokaryotic cells (e.g. *E. Coli*) include, but are not limited to pAYC184, pBeloBac11, pBR332, pBAD33, pBBR1MCS and its derivatives, pSC101, SuperCos (cosmid) and pWE15 (cosmid). Medium copy number expression vectors generally provide from about 20 to about 50 expression vectors copies per cell or from about 20 to 80 expression vectors copies per cell). Suitable medium copy expression vectors for prokaryotic cells (e.g. *E. Coli*) include, but are not limited to pTrc99A, pBAD24 and vectors containing a ColE1 origin of replication and its derivatives. High copy number expression vectors generally provide from about 80 to about 200 or more expression vector copies per cell. Suitable high copy expression vectors for prokaryotic cells (e.g. *E. Coli*) include, but are not limited to, pUC, PCV1, pBluescript, pGEM and pTZ vectors.

Aspects of the invention provide expression cassettes comprising a nucleic acid or a subsequence thereof encoding a polypeptide involved in the engineered pathway. In some embodiments, the expression cassette can comprise the nucleic acid that is operably linked to a transcriptional element (e.g. promoter) and to a terminator. As used herein, the term "cassette" refers to a nucleotide sequence capable of expressing a particular gene if said gene is inserted so as to be operably linked to one or more regulatory sequences present in the nucleotide sequence. Thus, for example, the expression cassette may comprise a desired heterologous gene to be expressed in the host cell. In some embodiments, one or more expression cassettes may be introduced into a vector by known recombinant techniques. A promoter is a sequence of nucleotides that initiates and controls the transcription of a desired nucleic acid sequence by an RNA polymerase enzyme. In some embodiments, promoters may be inducible. In other embodiments, promoters may be constitutive. Non limiting examples of suitable promoters for the use in prokaryotic host cells include a bacteriophage T7 RNA polymerase promoter, a trp promoter, a lac operon promoter and the like. Non limiting example of suitable strong promoter for the use in prokaryotic cells include lacUV5 promoter, T5, T7, Trc, Tac and the like. Non limiting examples of suitable promoters for use in eukaryotic cells include a CMV immediate early promoter, a SV40 early or late promoter, a HSV thymidine kinase promoter and the like. Termination control regions may also be derived from various genes native to the preferred hosts.

In some embodiments, a first enzyme of the engineered pathway may be under the control of a first promoter and the second enzyme of the engineered pathway may be under the control of a second promoter, wherein the first and the second promoter have different strengths. For example, the first promoter may be stronger than the second promoter or the second promoter may be stronger than the first promoter. Consequently, the level a first enzyme may be increased relative to the level of a second enzyme in the engineered pathway by increasing the number of copies of the first enzyme and/or by increasing the promoter strength to which the first enzyme is operably linked relative to the promoter strength to which the second enzyme is operably linked. In some other embodiments, the plurality of enzymes of the engineered pathway may be under the control of the same promoter. In other embodiments, altering the ribosomal binding site affects relative translation and expression of different enzymes in the pathway. Altering the ribosomal binding site can be used alone to control relative expression of enzymes in the pathway, or can be used in concert with the aforementioned promoter modifications and codon optimization that also affect gene expression levels.

In an exemplary embodiment, expression of the potential pathway enzymes may be dependent upon the presence of a substrate on which the pathway enzyme will act in the reaction mixture. For example, expression of an enzyme that catalyzes conversion of A to B may be induced in the presence of A in the media. Expression of such pathway enzymes may be induced either by adding the compound that causes induction or by the natural build-up of the compound during the process of the biosynthetic pathway (e.g., the inducer may be an intermediate produced during the biosynthetic process to yield a desired product).

In some embodiments, computer-implemented design techniques may be used to generate alternative pathways for generating an organic molecule of interest. In some embodiments, the databases contain information on genome and their link may be utilized for designing novel metabolic pathways. Examples of database are MetaCyc (a database of metabolic pathways and enzymes, the University of Minnesota biocatalysis/biodegradation database (a database of microbial catalytic reactions and biodegradation pathways for organic chemical compounds), LGAND (a composite database that provides information about metabolites and other chemical compounds, substrate-product relations representing metabolic and other reactions and information about enzyme molecules). A database of pathway components may also contain components of predicted, putative, or unknown functions. It may also contain pseudo-components of defined function that may have an undefined composition. In some embodiments, the program may design combinations of regulatory and/or functional elements that are in the public domain (e.g., that are not covered by patent rights and/or are not subject to a licensing fee). Databases of freely available genetic elements may be generated and/or used as a source of nucleic acid sequences that can be combined to produce alternative pathways. Alternative pathways containing different combinations of known functional and/or regulatory elements (e.g., from different species) may be designed, assembled, and/or tested. Libraries including variations in enzymatic element regions may be used to ascertain the relative effects of different types of enzymes or of different variants of the same enzyme. Libraries including variations in regulatory element regions may be used to ascertain the optimal expression level or regulatory control among a set of genes.

Nucleic acids encoding the different pathways may be assembled. In some embodiments, the functional properties of different engineered pathways may be tested in vivo by transforming host cells or organisms with the appropriate assembled nucleic acids, and assaying the properties of the engineered organisms. In some embodiments, the functional properties of different engineered pathways may be tested in vitro by isolating components expressed from assembled nucleic acids and testing the appropriate combinations of components in an in vitro system.

I. Engineered Coenzyme B Synthesis Pathway for the Production of 2-Keto Acids (C5 to C8)

Figure 1B:
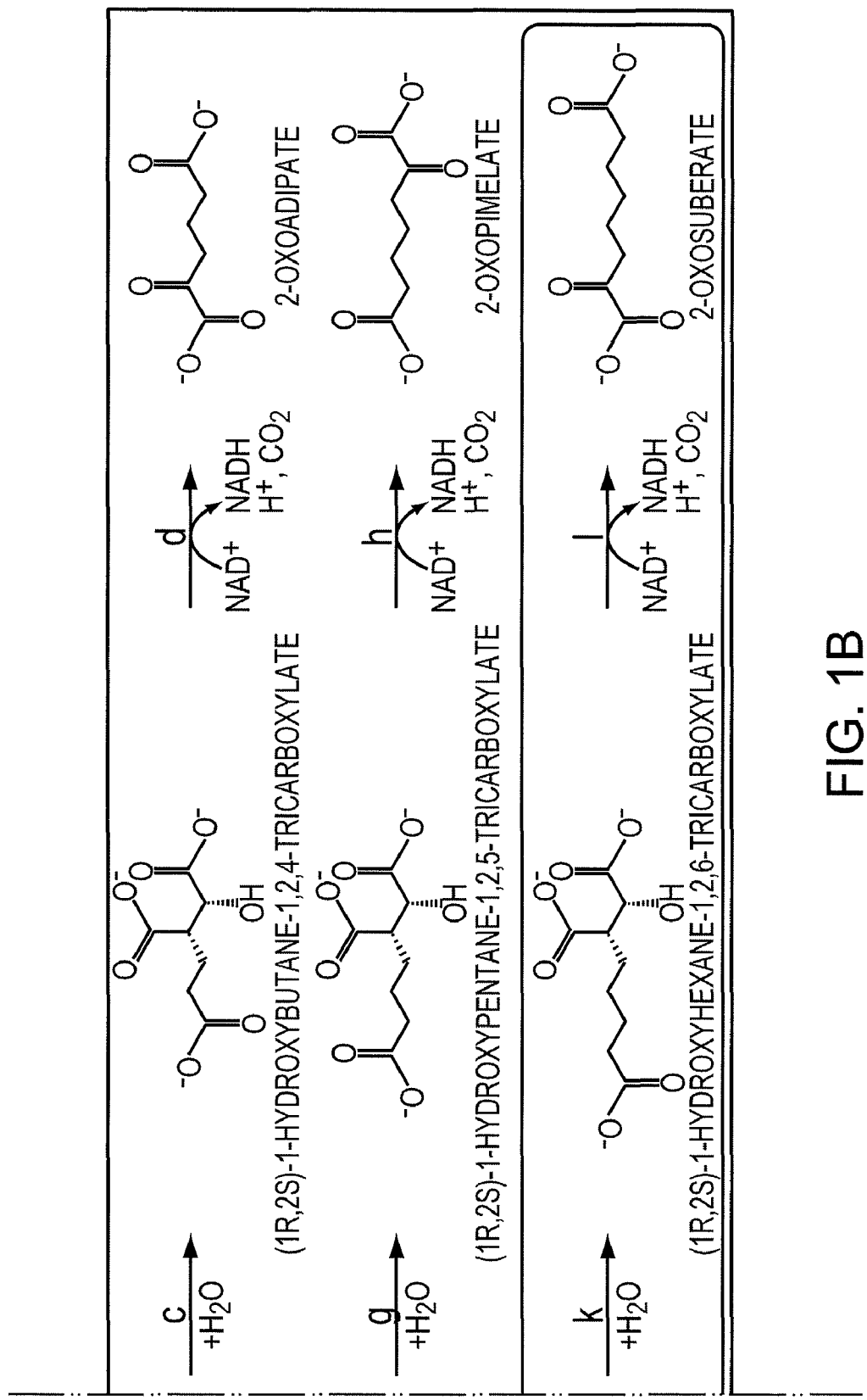

Aspects of the invention provides novel engineered routes for the production of difunctional n-alkanes via α-keto acid chain elongation reactions involved in the biosynthesis of Coenzyme B (see FIG. 1). As used herein α-keto acids or 2-oxo acids or 2-keto acids are used interchangeably and design organic acids containing a ketone functional group adjacent to a carboxylic acid group. The α-keto acid chain elongation reactions (also called 2-oxo acid elongation) involved in the biosynthesis of Coenzyme B is used herein to refer to the biosynthetic pathway that convert α-ketoglutarate (C5 chain) and acetylCoA to α-ketosuberate (C8 chain), a precursor to the coenzyme B (7-mercapto heptanoylthreonine phosphate) and possibly biotin. Many organisms can synthesize α-ketoglutarate via oxaloacetate produced from either PEP via the enzyme PEP carboxylase, or from pyruvate via the biotin-dependent enzyme pyruvate carboxylase. α-ketoglutarate is a key intermediate in the Krebs cycle and serves as input to a α-keto acid elongation pathway. The α-keto acid elongation coenzyme B pathway comprises enzymes that catalyze the following steps:

(1) condensation of α-ketoglutarate and acetylCoA to form homocitrate (e.g. by action of a homocitrate synthase such as for example AksA, NifV, Hcs, Lys 20/21)

(2) dehydration and hydration to (2R,3S) homoisocitrate with cis homoaconitate serving as an intermediate (e.g. by action of a homoaconitase such as for example AskD/E, LysT/U, Lys4,3-isopropylmalate dehydratase)

(3) Oxidative decarboxylation of (2R,3S) homoisocitrate to α-ketoadipate (e.g. by action of homoisocitrate dehydrogenase such as for example AksF, Hicdh, Lys12, 2-oxosuberate synthase, 3-isoprpopylmalate dehydrogenase).

The resulting α-ketoadipate (C6 chain) then undergoes two consecutive sets of α-keto acid chain elongation reactions to produce the α-ketopimelate as an intermediate and α-ketosuberate. The α-ketosuberate resulting from this series of reactions then undergoes a non-oxidative decarboxylation to form 7-oxoheptanoic acid, a precursor to coenzyme B.

One well-characterized example of the α-keto acid elongation pathway is the Coenzyme B biosynthesis pathway of *Methanococcus jannaschii*. In this pathway, there are three enzymes catalyzing steps a-l in FIG. 1. AksA (catalyzing steps a, e, and i) is a homocitrate synthase; AksD/E (catalyzing steps b, c, f, g, j, k) is a heterotetramer of AksD and AksE, and is a homoaconitase; AksF (catalyzing steps d, h, and l) is a homoisocitrate dehydrogenase. These enzymes have all been shown to catalyze the reaction steps and *M. jannaschii* AksD/E is the only homoaconitase that has been shown to catalyze both hydrolyase reactions to date (Howell et al., Biochem., 1998; Howell et al., J. Bacteriol., 2000; Drevland et al., JBC, 2008). One should note that *M. jannaschii* is a thermophilic methanogen, and all of the Aks enzymes have been characterized at 50-60° C. In some embodiments, alternative Aks homologs from other methanogens that propagate at 37° C. may be used. Such Aks homologs have been identified and include *Methanococcus maripaludis* S2 genes aksA (MMP0153), MMP1480, MMP0381, and aksF (MMP0880).

The pathway starting with α-ketoglutarate (C5) has the different following intermediates depending of the number of elongation rounds: α-ketoadipate (C6), α-ketopimelate (C7) and α-ketosuberate (C8). Consequently, in some aspects of the invention, depending on the hydrocarbon chain length (e.g. C4, C5, C6, C7) of the desired product, no elongation (for difunctional butane production), only a single elongation round (e.g. steps a through d, for difunctional pentane production), two elongations (e.g. steps a through h, for difunctional hexane production) or three elongations (e.g. steps a though 1, for difunctional heptane production) may be required. One should therefore appreciate that, depending of the hydrocarbon chain length, it may be desirable to maximize the availability of either the 2-ketoadipate intermediate or the ketopimelate intermediate. In some embodiments, it is desirable to keep steps a through d and eliminate steps e through 1 in order to maximize the availability of the 2-keto adipate intermediate. In other embodiments, it may be desirable to keep steps a through h and eliminate steps i through 1 to maximize the availability of the ketopimelate intermediate.

As described above, each elongation step comprises a set of three enzymes: an acyltransferase or acyltransferase homolog, a homoaconitase or homoaconitase homolog, and a homoisocitrate dehydrogenase or homoisocitrate dehydrogenase homolog. The first reaction of each elongation step is catalyzed by an acetyl transferase enzyme that converts acyl groups into alkyl groups on transfer. In some embodiments, the acyl transferase enzyme is a homocitrate synthase (EC 2.3.3.14). Homocitrate synthase enzymes that catalyze the chemical reaction acetyl-CoA+H2O+2-oxoglutarate⇌(R)-2-hydroxybutane-1,2,4-tricarboxylate+CoA.

The product (R)-2-hydroxybutane-1,2,4-tricarboxylate is also known as homocitrate. It has been shown that some homocitrate synthases, such as AksA, have a broad substrate range and catalyse the condensation of oxoadipate and oxopimelate with acetyl CoA (Howell et al., 1998, Biochemistry, Vol. 37, pp 10108-10117). Some aspects of the invention provide a homocitrate synthase having a substrate specificity for oxoglutarate or for oxoglutarate and for oxoadipate. Preferred homocitrate synthase are known by EC number 2.3.3.14. In general, the process for selection of suitable enzymes may involve searching enzymes among natural diversity by searching homologs from other organisms and/or creating and searching artificial diversity and selecting variants with selected enzyme specificity and activity. Candidate homocitrate synthases, candidate homoaconitases and candidate homoisocitrate dehydrogenase are listed in Table 1.

TABLE 1

| Step | Activity | Candidate enzymes |
| --- | --- | --- |
| a | homocitrate synthase | AksA, NifV, Hcs, Lys20/21 |
| b | homoaconitase | AksD/E, LysT/U, Lys4, 3-isopropylmalate dehydratase Large/Small |
| c | homoaconitase | AksD/E, LysT/U, Lys4, 3-isopropylmalate dehydratase Large/Small |
| d | homoisocitrate dehydrogenase | AksF, Hicdh, Lys 12, 2-oxosuberate synthase, 3-isopropylmalate dehydrogenase |
| e | Homo2citrate synthase | AksA, NifV |
| f | Homo2aconitase | AksD/E, 3-isopropylmalate dehydratase Large/Small |
| g | Homo2aconitase | AksD/E, 3-isopropylmalate dehydratase Large/Small |
| h | Homo2isocitrate dehydrogenase | AksF, 2-oxosuberate synthase, 3-isopropylmalate dehydrogenase |
| i | Homo3citrate synthase | AksA |
| j | Homo3aconitase | AksD/E, 3-isopropylmalate dehydratase Large/Small |
| k | Homo3aconitase | AksD/E, 3-isopropylmalate dehydratase Large/Small |
| l | Homo3isocitrate dehydrogenase | AksF, 2-oxosuberate synthase, 3-isopropylmalate dehydrogenase |

In some embodiments, the first step of the pathway is engineered to be catalyzed by the homocitrate synthase NifV or NifV homologs. Homologs of NifV are found in a variety of organisms including but not limited to *Azotobacter vinelandii, Klebsiella pneumoniae, Azotobacter chroococcum, Frankia* sp. (strain FaCl), *Anabaena* sp. (strain PCC 7120), *Azospirillum brasilense, Clostridium pasteurianum, Rhodobacter sphaeroides, Rhodobacter capsulatus, Frankia alni, Carboxydothermus hydrogenoformans* (strain Z-2901/DSM 6008), *Anabaena* sp. (strain PCC 7120), *Frankia alni, Enterobacter agglomerans, Erwinia carotovora* subsp. *atroseptica* (*Pectobacterium atrosepticum*), *Chlorobium tepidum, Azoarcus* sp. (strain BH72), *Magnetospirillum gryphiswaldense, Bradyrhizobium* sp. (strain ORS278), *Bradyrhizobium* sp. (strain BTAi1/ATCC BAA-1182), *Clostridium kluyveri* (strain ATCC 8527/DSM 555/NCIMB 10680), *Clostridium kluyveri* (strain ATCC 8527/DSM 555/NCIMB 10680), *Clostridium butyricum* 5521, *Cupriavidus taiwanensis*

(strain R1/LMG 19424), *Ralstonia taiwanensis* (strain LMG 19424), *Clostridium botulinum* (strain Eklund 17B/type B), *Clostridium botulinum* (strain Alaska E43/type E3), *Synechococcus* sp. (strain JA-2-3B' a(2-13)) (Cyanobacteria bacterium Yellowstone B-Prime), *Synechococcus* sp. (strain JA-3-3Ab) (Cyanobacteria bacterium Yellowstone A-Prime), *Geobacter sulfurreducens* and *Zymomonas mobilis*. NifV has been shown to use oxoglutarate (enzymatic step a) and oxoadipate (enzymatic step e) as a substrate but not but has not been demonstrated to use oxopimelate as a substrate (see Zheng et al., (1997) J. Bacteriol. Vol. 179, pp 5963-5966). Consequently, engineered 2-keto-elongation pathway comprising the homocitrate synthase NifV eliminates steps i through l in the 2-ketoelongation pathway and maximizes the availability of 2-ketopimelate intermediate.

In some embodiments, the first step of the pathway is engineered to be catalyzed by the homocitrate synthase Lys2 0 or Lys 21. Lys 20 and Lys 21 are two homocitrate synthase isoenzymes implicated in the first step of the lysine biosynthetic pathway in the yeast *Saccharomyces cerevisiae*. Homologs of Lys 20 or Lys 21 are found in a variety of organisms such as *Pichia stipitis* and *Thermus thermophilus*. Lys20 and Lys21 enzymes have been shown to use oxoglutarate as substrate but not to use oxoadipate or oxopimelate. Consequently, engineered 2-ketoelongation pathway comprising Lys20/21 eliminates steps e through l in the 2-ketoelongation pathway and maximized the availability of 2-oxoadipate. In some embodiments, enzymes catalyzing the reaction involving acetyl coenzyme A and α-keto acids as substrates are used to convert a-keto acid into homocitrate (e.g. EC 2.3.3.-). Methanogenic archaea contain three closely related homologs of AksA: 2-isopropylmalate synthase (LeuA) and citramalate (2-methylmalate) synthase (CimA) which condenses acetyl-CoA with pyruvate. This enzyme is believed to be involved in the biosynthesis of isoleucine in methanogens and possibly other species lacking threonine dehydratase. In some embodiments, the acyl transferase enzyme is an isopromylate synthase (e.g. LeuA, EC 2.3.3.13) or a citramalate synthase (e.g. CimA, EC 2.3.1.182).

The second step of the keto elongation pathway is catalyzed by a homoaconitase enzyme. The homoaconitase enzyme catalyzes the hydratation and dehydratation reaction:

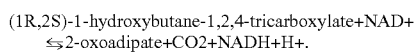

homocitrate ⇌ cis-homoaconitate + H₂O

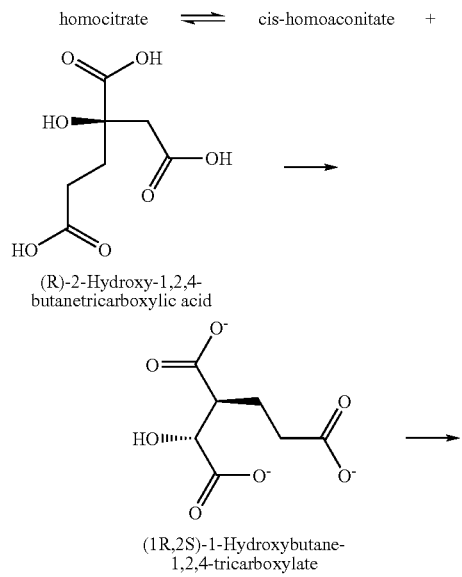

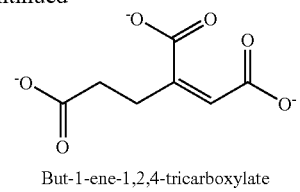

But-1-ene-1,2,4-tricarboxylate

In some embodiments, the homoaconitase is AksD/E, lysT/U or lys4 or homologs or variants thereof. Homoaconitases AksD/E and lysT/U have been shown to consist of two polypeptides AksD and AksE, lysT and lysU, respectively.

The last step of each keto elongation cycle is catalyzed by a homoisocitrate dehydrogenase. A homoisocitrate dehydrogenase (e.g. EC 1.1.1.87) is an enzyme that catalyzes the chemical reaction (1R,2S)-1-hydroxybutane-1,2,4-tricarboxylate+NAD+ ⇌ 2-oxoadipate+CO2+NADH+H+.

In some embodiments, the homocitrate dehydrogenase includes, but is not limited to, AksF, Hicdh, lys12, and LeuB (EC1.1.1.85). LeuB is 3-isopropylmalate dehydrogenase (EC1.1.1.85) (IMDH) and catalyzes the third step in the biosynthesis of leucine in bacteria and fungi, the oxidative decarboxylation of 3-isopropylmalate into 2-oxo-4-methylvalerate. It has been shown that 2-ketoisovalerate is converted to 2-ketoisocaproate through a 3 step elongation cycle by LeuA (2-isopropylmalate synthase), LeuC, LeuD (3-isopropylmalate isomerase complex) and LeuB (3-isopropylmalate dehydrogenase) in the leucine biosyntheis pathway. One should appreciate that these enzymes have broad substrate specificity (see Zhang et al., (2008), P.N.A.S) and may catalyze the α-ketoacid elongation reactions. In some embodiments, LeuA, LeuC, LeuD and LeuB catalyze the elongation of α-ketoglutarate to α-ketoadipate and the elongation of α-ketoadipate to α-ketopimelate.

II. Engineered Pathways for the Production of Difunctional Alkanes (C4 to C7) from the α-Keto Acids (C5 to C8)

Figure 2:
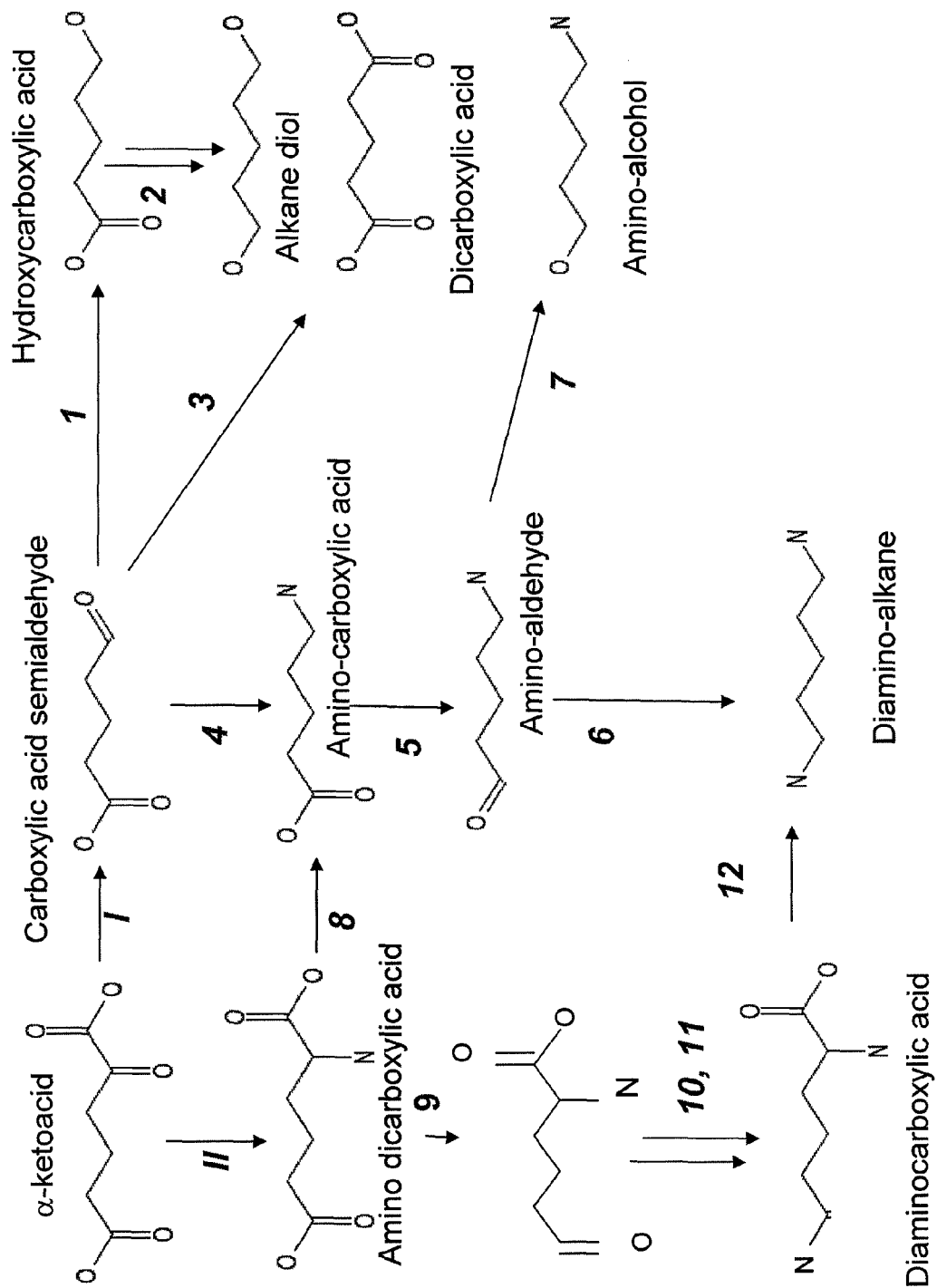
FIG. 2 represents a flow diagram for the bioproduction of difunctional alkanes C(n−1) starting from an α-keto acid Cn.

There are several potential pathways for production of difunctional alkanes from α-keto acids sources with recombinant microorganisms as shown in FIG. 2. Aspects of the invention relate to bioconversion of the α-keto intermediates into difunctional butane, difunctional pentane, difunctional hexane, difunctional heptane molecules. Difunctional butane molecules of interest include, but are not limited to, 1,4-butane diol, 1-hydroxybutanoate, succinic acid, 1,4-diaminobutane, 4-aminobutanal and 4-aminobutanol. Difunctional pentane molecules of interest include, but are not limited to, 1-hydroxypentanoate, 1,5-pentanediol, glutarate, cadaverine (pentane-1,5-diamine), 5-aminopentanal and 5-aminopentanol. Difunctional hexane molecules of interest include, but are not limited to, 1-hydroxyhexanoate, 1,6-hexanediol, adipate, hexamethylenediamine, amino caproic acid, 6-amino hexanal and 6-aminohexanol. Difunctional heptane molecules of interest include but are not limited to 1-hydroxyheptanoate, 1,7-heptanediol, pimelic acid, 1,7-diaminoheptane, 7-aminoheptanal and 7-aminoheptanol.

In some embodiments, the first potential pathway for the production of difunctional alkanes includes first a α-keto acid decarboxylation (enzymatic step I). Some aspects of the present invention disclose a method for removing the carboxylic group by non oxidative decarboxylation. This is accomplished by expressing in a host cell a protein having a biological activity substantially similar to a α-keto acid decarboxylase to generate a carboxylic acid semialdehyde. The term "α-keto acid decarboxylase" (KDCs) refers to an enzyme that catalyzes the conversion of α-ketoacids to carboxylic acid semialdehyde and carbon dioxide. Some KDCs of particular interest are known by the EC following numbers: EC 4.1.1.1; EC 4.1.1.80, EC 4.1.1.72, 4.1.1.71, 4.1.1.7, 4.1.1.75, 4.1.1.82, 4.1.1.74 (see table 2 below). Some of the KDCs have wide substrate range whereas other KDCs are more substrate specific. KDCs are available from a number of sources, including but not limited to, *S. cerevisiae* and bacteria. In some exemplary embodiments, the KDCs used include but are not limited to KivD from *Lactococcus lactis* (UniProt Q684J7), ARO10 (UniProt Q06408) from *S. cerevisiae*, PDC1 (UniProt P06169), PDC5 (UniProt P16467), PDC6 (UniProt P26263), Thi3 from *S. cerevisiae*, kgd from *M. tuberculosis* (UniProt 50463), mdlc from *P. putida* (UniProt P20906), azu1 from *P. aeruginosa* (UniProt AAG08362), fom2 from *S. wedmorensis* (UniProt Q56190), Pdc from *Clostridium acetobutyculum*, ipdC from *E. coacae* (UniProt P23234) or any homologous proteins from the same or other microbial species. In some embodiments, the keto acid decarboxylase is a pyruvate decarboxylase known by the EC number EC 4.1.1.1. Pyruvate decarboxylase are enzymes that catalyzes the decarboxylation of pyruvic acid to acetaldehyde and carbon dioxide. Pyruvate decarboxylases are available from a number of sources including but not limited to, *S. cerevisiae* and bacteria (see US Patent 20080009609 which are incorporated hereien by reference). In some embodiments, the α-keto acid decarboxylase is the α-ketoisovalerate decarboxylase KivD that naturally catalyzes the conversion of α-ketoisovalerate to isobutyraldehyde and carbon dioxide. In some embodiments, α-keto acid decarboxylase is a branched chain α-keto acid decarboxylases (EC number 4.1.1.72). One should appreciate that since some of the KDCs have been shown to have a broad substrate range, substrate specificity may be an important consideration when selecting the gene sources. Therefore, in some embodiments, pyruvate decarboxylase enzymes are engineered to show a preference for α-ketosuberate, α-ketopimelate, α-ketoadipate or α-ketoglutarate over pyruvate. Preferably, the engineered enzyme shows at least a 2 fold, at least a 5 fold, at least a 10 fold, at least a 20 fold, at least a 50 fold, at least a 100 fold increase preference over pyruvate.

In preferred embodiments, the KDC expressed in the recombinant host cells catalyses the conversion of α-ketosuberate to pimelic acid semialdehyde, or the conversion of α-ketopimelate to adipic acid semialdehyde, or the conversion of α-ketoadipate to glutaric acid semialdehyde, or the conversion of α-ketoglutarate to succinic acid semialdehyde.

In some embodiments, the carboxylic acid semialdehyde (e.g. succinic acid semialdehyde, glutaric acid semialdehyde, adipic acid semialdehyde and/or pimelic acid semialdehyde) is converted into hydroxyl carboxylic acid (hydroxyl butanoate, hydroxypentanoate, hydroxyhexanoate, hydroxyheptanoate) by an alcohol dehydrogenase that converts the aldehyde functional group into an alcohol functional group (enzymatic step 1, FIG. 2). Alcohol dehydrogenases (ADHs) (EC 1.1.1.1 and EC 1.1.1.2) catalyze the reversible reduction of ketones and aldehydes to alcohols with the reduction of NAD+ to NADH. In some embodiments, the alcohol dehydrogenase includes, but is not limited to, adhA or adhB (from *Z. mobilis*), butanol dehydrogenase (from *Clostridium acetobutylicum*), propanediol oxidoreductase (from *E. coli*), and ADHIV alcohol dehydrogenase (from *Saccharomyces*), or ADH6 (from *S. cerevisiae*).

In some embodiments, the hydro-carboxylic acid is subjected to dehydrogenation using an alcohol dehydrogenase or an aldehyde dehydrogenase (enzymatic step 2, FIG. 2 and FIG. 3) to produce an alkane diol such as 1,4-butane diol, 1,5-pentane diol, 1,6-hexane diol, and/or 1,7-heptanediol.

Aldehyde NAD(+) dehydrogenase activity and alcohol NAD(+) dehydrogenase activities can be carried out by two different polypeptides, or carried out by a single polypeptide, such as a multi-functional aldehyde-alcohol dehydrogenase (EC 1.2.1.10) from *E. coli* (Goodlove et al. Gene 85:209-14, 1989; GenBank Accession No. M33504). Polypeptides having aldehyde dehydrogenase (NAD(P)+) (EC 1.2.1.-) or aldehyde dehydrogenase (NAD(+)) (EC 1.2.1.3) activity can be used in combination with an alcohol dehydrogenase to reduce the remaining carboxylic acid to an alcohol, yielding an alkane diol. Nucleic acid encoding such polypeptides can be obtained from various species including, without limitation, *S. cerevisiae*.

In other embodiments, the carboxylic acid semialdehyde (e.g. succinic acid semialdehyde, glutaric acid semialdehyde, adipic acid semialdehyde, pimelic acid semialdehyde) is converted into a dicarboxylic acid (enzymatic step 3, FIG. 2 and FIG. 3) such as adipic acid, succinic acid, glutaric acid and/or pimelic acid through the use of an aldehyde dehydrogenase.

In one aspect of the invention, the initial α-keto acid decarboxylation step is followed by a 1-aminotransferase enzymatic step (enzymatic step 4, FIG. 2 and FIG. 3) for the production of an amino carboxylic acid. Particularly, interesting product that may be synthesized using this engineered pathway include amino caproic acid, amino butanoic acid, aminoheptanoic acid and/or aminopentanoic acid. In some embodiments, enzymatic step 4 contains a carboxylic acid semialdehyde aminotransferase. Enzymes having a carboxylic acid semialdehyde aminotransferase activity are available from a number of sources include, but not limited to *B. subtilis, S. cerevisiae. H. sapiens, F. lutescens, S. clavuligerus*. Exemplary enzymes capable to catalyze the amino transferase reactions are the ornithine-oxo-acid transaminase (rodD from *B. subtilis*, OAT from *H. sapiens*, EC 2.6.1.13), arginine-degradative enzyme ornithine transaminase (EC 2.6.1.13), Lysine-aminotransferase (EC 2.6.1.36) from *F. lutescens* or *S. clavuligerus, Mus musculus* 4-aminobutyrate aminotransferase (EC 2.6.1.19), *Sus scrofa* 4-aminobutyrate aminotransferase (EC 2.6.1.19), *S. cerevisiae* 4-aminobutyrate aminotransferase (EC 2.6.1.19), *S. cerevisiae* Saccharopine dehydrogenase LYS9 and LYS1 (EC 1.5.1.10 and 1.5.1.7 respectively) or any homologous proteins from the same or other microbial species.

Two potential pathways for the production of diamino alkanes or amino alcohol of interest include the conversion of the amino carboxylic acid into an amino-aldehyde using an aldehyde dehydrogenase (enzymatic step 5, FIG. 2 and FIG. 3) followed by enzymatic step 6 or enzymatic step 7. In another embodiment, the 2-aminodicarboxylic acid may be subjected to a 2-aminodecarboxylase (enzymatic step 8) generating an aminocarboxylic acid. In some embodiments, enzymatic step 8 is followed by a dehydrogenation step catalyzed by and aldehyde dehydrogenase (enzymatic step 5). The resulting aminoaldehyde metabolite may be used as a substrate for two different enzymatic steps. Enzymatic step 6 includes a 1-amino transferase and catalyzes the conversion of the amino-aldehyde to a diamino alkane. Alternatively, enzymatic step 7 including an alcohol dehydrogenase catalyzes the conversion of the amino-aldehyde to an amino-alcohol. Enzymatic step 6 includes an amino transferase enzyme and produces diamino alkanes such as hexamethylenediamine (HDD), cadaverine (or pentamethylenediamine), diaminobutane, and/or dimaminoheptane. Enzymatic step 7 includes a alcohol dehydrogenase and produce aminobutanol, aminopentanol, aminohexanol (or 6 hydroxyhexamine 6HH), and aminoheptanol.

The second potential pathway includes first a 2-amino transferase (enzymatic step II, FIG. 2 and FIG. 3) generating a 2 amino dicarboxylic acid. Preferred candidate genes of interest that express an aminotransferase activity include, but are not limited to, lysN (encoding an α-aminoadipate aminotransferase from *T. thermophilus* EC 2.6.1.7) and homologs (e.g. kat2); aadat (encoding an amino adipate aminotransferase in *R. norvegicus*, EC 2.6.1.39), AADAT (encoding an amino adipate aminotransferase in *H. sapiens*). Alternate enzymes having an aminotransferase activity include, but are not limited to ddh (from *Corynebacterium glutanicum*, encoding a meso-diaminopimelate D-dehydrogenase, EC 1.4.1.16) and dapdh (from Lysinibacillus sphaericus encoding a meso-diaminopimelate dehydrogenase, EC 1.4.1.16). Candidate genes expressing an aminopimelate decarboxylase activity include, but are not limited to, glutamate decarboxylases (EC 4.1.1.15), for example, gadA/B, encoding isoform A or isoform B in *E. coli*, GAD1 (from *S. cerevisiae*), GAD1/2 (from *A. thaliana*), GAD1/2 (from *H. sapiens*) and their homologs or to diaminopimelate decarboxylase such as for example LysA (EC 1.1.1.20, from *E. Coli* or *Bacillus subtilis*) or AT5G11880 (from *A. thaliana*) or AT3G14390 (from *A. thaliana*).

Figure 3:
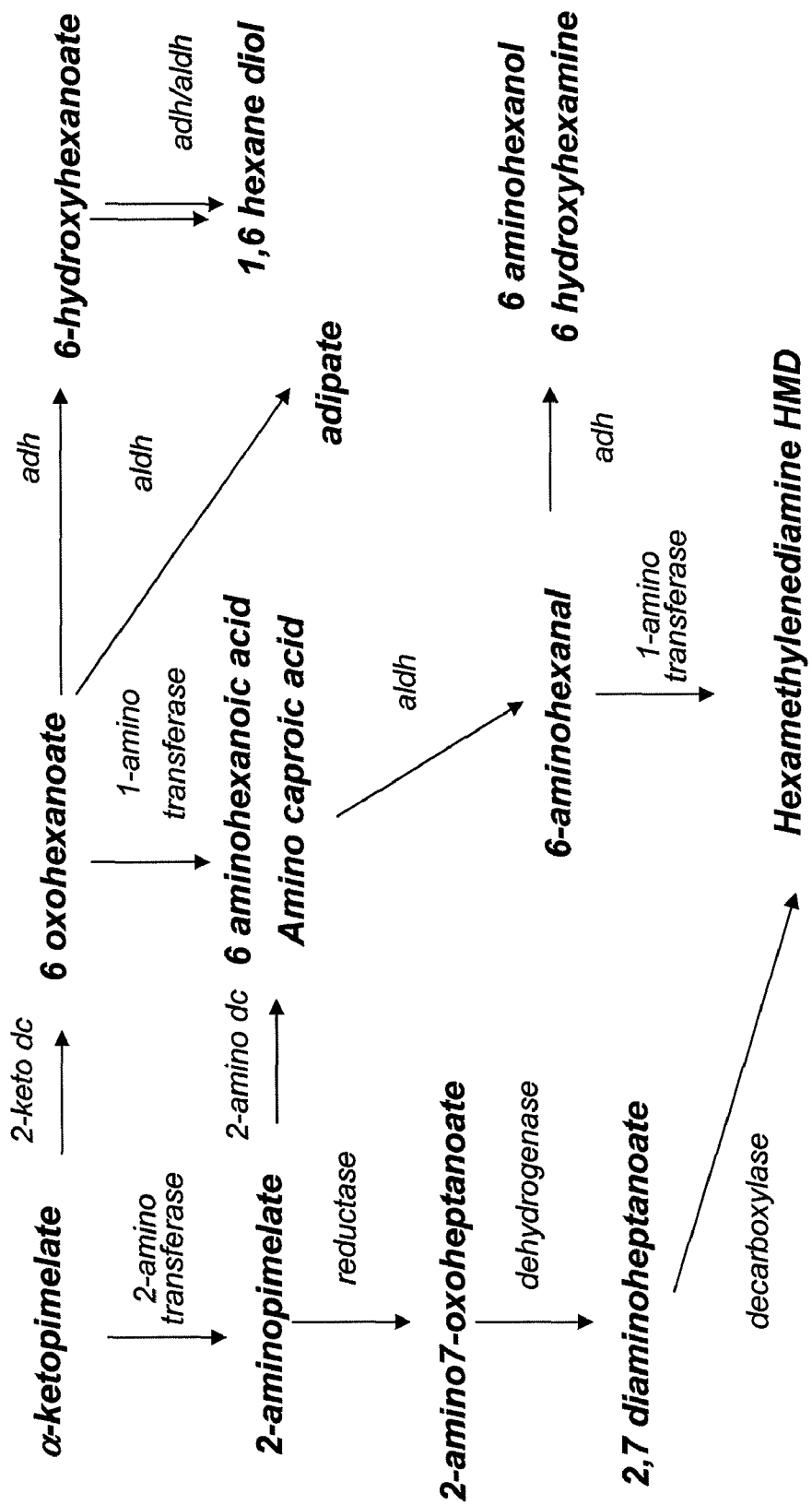
FIG. 3 represents a flow diagram for the bioproduction of difunctional hexanes starting from 2-ketopimelate.

III. Engineered Pathways for the Production of C6 Difunctional Alkanes from α-Ketopimelate Aspects of the invention relate to the engineered pathways for the production of C6 difunctional alkanes of interest. Particularly, aspects of the invention relates to the production of adipic acid, amino caproic acid (a stable precursor of caprolactam acid), hexamethylene diamine and 6-hydroxyhexanoate (FIG. 3). One should appreciate that for the bioproduction of C6 difunctional alkanes, it is desirable to eliminate steps i through l in order to maximize the availability of 2-ketopimelate for bioconversion to adipate semialdehyde (step m). In some embodiments, AksA is substituted with NifV, an enzyme from *A. vinelandii* that has been shown to act on both 2-ketoglutarate and 2-ketoadipate, but not 2-ketopimelate (Howell et al., Biochem., 1998; Howell et al., J. Bacteriol., 2000; Drevland et al., JBC, 2008). Such a substitution would eliminate steps i through l in the 2-keto acid elongation pathway. One should appreciate that depending on the hydrocarbon chain length of the desired product, only a single elongation round (e.g. steps a-d) may be required. In some exemplary embodiments, glutaric acid, a common plasticizer and a precursor to polyesters, with the formula HO2C(CH2)3CO2H (also named pentanedioic acid) may be bioproduced from 2-ketoglutarate that was subjected to a single elongation round to produce ketoadipate. Glutaric acid is used in the production of polymers such as polyester polyols, and polyamides. In some embodiments, to enable single round elongation, Hcs and Lys20/21 enzymes (from the lysine biosynthesis pathways of *S. cerevisiae* and *T. thermophilus*) may enable elimination of steps e-l in order to maximize the viability of 2-ketoadipate for the bioproduction of glutaric acid.

A. Engineered Pathways for the Production of Adipic Acid

1. Overview on Adipic Acid:

In 2005, global demand for adipic acid was 2.7 million metric tons. Historically the demand for adipic acid has grown 2% per year and a 2-3% increase is expected through the year 2009. Adipic acid consistently ranks as one of the top fifty chemicals produced in the US. Nearly 90% of domestic adipic acid is used to produce nylon-6,6. Other uses of adipic acid include production of lubricants resins, polyester polyols and plasticizers, and as a food acidulant.

There are three major commercial production processes: cyclohexane process, cyclohexanol process, butadiene carbonylation process. The dominant industrial process for synthesizing adipic acid employs initial air oxidation of cyclohexane to yield a mixture of cyclohexanone (ketone) and cyclohexanol (alcohol), which is designated KA (see for example U.S. Pat. No. 5,221,800). Hydrogenation of phenol to yield KA is also used commercially, although this process accounts for just 2% of all adipic acid production. KA produced via both methods is oxidized with nitric acid to produce adipic acid. Reduced nitrogen oxides including NO2, NO, and N2O are produced as by-products and are recycled back to nitric acid at varying levels. It is becoming increasingly more interesting to industry and beneficial to the environment to engineer non-synthetic, biological routes to adipic acid. A number of microbiological routes have been described. Wild-type and mutant organisms have been shown to convert renewable feedstocks such as glucose and other hydrocarbons to adipic acid (see for example WO9507996, and U.S. Pat. Nos. 5,272,073, 5,487,987 and 5,616,496). Similarly, organisms possessing nitrilase activity have been shown to convert nitriles to carboxylic acids including adipic acid (see for example U.S. Pat. No. 5,629,190). Additionally, wild-type organisms have been used to convert cyclohexane and cyclohexanol and other alcohols to adipic acid (see for example U.S. Pat. No. 6,794,165; and US Patent Applications Nos 2003087403 and 20020127666). For example, in one enzymatic pathway, cyclohexanol is converted in adipic acid, the enzymatic pathway comprising genes isolated from an *Acinetobacter* encoding hydroxylacylCoA dehydrogenase; enoyl-CoA hydratase, acylCoA dehydrogenease, ubiqunone oxidoreductase, monoxygenase, aldehyde dehydrogenase. Another enzymatic pathway for the conversion of cyclohexanol to adipic acid has been suggested as including the intermediates cyclohexanol, cyclohexanone, 2-hydroxycyclohexanone, ε-caprolactone, 6-hydroxycaproic acid. Some specific enzyme activities in this pathway have been demonstrated, including cyclohexanol dehydrogenase, NADPH-linked cyclohexanone oxygenase, ε-caprolactone hydrolase, and NAD (NADP)-linked 6-hydroxycaproic acid dehydrogenase (Tanaka et al., Hakko Kogaku Kaishi (1977), 55(2), 62-7). An alternate enzymatic pathway has been postulated to comprise cyclohexanol, cyclohexanone, 1-oxa-2-oxocycloheptane, 6-hydroxyhexanoate, 6-oxohexanoate and adipate (Donoghue et al., Eur. J. Biochem., 1975, 60(1), 1-7).

The problem to be solved therefore is to provide a synthesis route for adipic acid which not only avoids reliance on environmentally sensitive starting materials such as petroleum but also makes efficient use of non-petrochemical inexpensive, renewable resources. It would further be desirable to provide a synthesis route for adipic acid which avoids the need for significant energy inputs and which minimizes the formation of toxic by-products.

2. Adipic Acid Bioproduction Via the α-Ketopimelate Route

Some aspects of the invention relate to the decarboxylation of 2-ketopimelate to adipate semialdehyde (or 6-oxohexanoate) and the dehydrogenation of adipate semialdehyde to produce adipic acid. In some embodiments, all published MetaCyc decarboxylase reactions were screened for candidate 2-ketopimelate decarboxylases. A list of enzymes and activities was generated based on the criteria (i) demonstrated activity on a 2-ketocarboxylate and (ii) availability of protein sequence information (see Table 2). In some embodiments, the enzymes listed in Table 2 are screened for decarboxylase activity on all 2-keto acids in the proposed engineered pathways (i.e. 2-ketopimelate, 2-ketoadipate, and 2-ketoglutarate).

TABLE 2

| | Desired substrate and product | 2-ketopimelate ⇌ adipate semialdehyde + CO₂ |
|---|---|---|

| | | |
|---|---|---|
| EC 4.1.1.71<br>2-ketoglutarate decarboxylase<br>kgd from *M. tuberculosis*<br>UniProt: O50463 | | 2-ketoglutarate ⇌ succinate semialdehyde + CO₂ |
| EC 4.1.1.1<br>2-ketoisovalerate decarboxylase<br>kivD from *L. lactis*<br>UniProt: Q684J7 | | 2-keto-isovalerate ⇌ isobutanal + CO₂ |
| EC 4.1.1.43<br>Transaminated a.a. decarboxylase<br>ARO10 from *S. cerevisiae*<br>UniProt: Q06408 | | phenylpyruvate ⇌ CO₂ + phenylacetaldehyde |
| EC 4.1.1.7<br>Benzoylformate decarboxylase<br>mdlC from *P. putida*<br>crystal structure available<br>UniProt: P20906 | | 2-oxo-2-phenylacetate ⇌ CO₂ + benzaldehyde |
| EC 4.1.1.75<br>2-ketoarginine decarboxylase<br>aruI; *P. aeruginosa*<br>NCBI AAG08362 | | 2-ketoarginine ⇌ CO₂ + 4-guanidinobutyraldehyde |
| EC 4.1.1.82<br>Phosphonopyruvate decarboxylase<br>fom2; *Streptomyces wedmorensis*<br>UniProt: Q56190<br>NCBI AB016934 | | 3-phosphonopyruvate ⇌ phosphonoacetaldehyde + CO₂ |

TABLE 2-continued

| | | |
|---|---|---|
| Desired substrate and product | 2-ketopimelate | adipate semialdehyde + CO$_2$ |
| EC 4.1.1.80<br>Pyruvate decarboxylase isozyme<br>PDC6, PDC1; *S. cerevisiae*<br>PDC1 crystal structure available<br>PDC1 UniProt: P06169<br>PDC6 UniProt: P26263 | 4-hydroxyphenylpyruvate | (4-hydroxyphenyl) acetaldehyde + CO$_2$ |
| EC 4.1.1.1<br>Pyruvate decarboxylase isozyme 2<br>PDC5, *S. cerevisiae*<br>(also, PDC1, PDC6, Aro10, KivD)<br>UniProt: P16467 | a 2-oxo acid | an aldehyde + CO$_2$ |
| EC 4.1.1.74<br>Indolepyruvate decarboxylase<br>ipdC; *Pantoea agglomerans*<br>ipdC; *Enterobacter cloacae*<br>*P.a.* UniProt P71323<br>*E.c.* UniProt P23234 | indole-3-pyruvate | indole acetaldehyde + CO$_2$ |
| EC 4.1.1.74<br>Indolepyruvate decarboxylase<br>ipdC; *Pantoea agglomerans*<br>ipdC; *Enterobacter cloacae*<br>*P.a.* UniProt P71323<br>*E.c.* UniProt Q47305 | indole-3-pyruvate | indole acetaldehyde + CO$_2$ |
| EC 4.1.1.40<br>hydroxypyruvate decarboxylase<br>gene unknown | hydroxypyruvate | glycolaldehyde + CO$_2$ |

In a preferred embodiment, the conversion of adipate semialdehyde to adipate (step n) is catalyzed using a ChnE enzyme or a homolog of the ChnE enzyme. ChNE is an NADP+-linked 6-oxohexanoate dehydrogenase enzyme and has been to shown to catalyze the dehydrogenation of the 6-oxohexanoate to adipate in the cyclohexanol degradation pathway in *Acinetobacter* sp. (see Iwaki et al., Appl. Environ. Microbiol. 1999, 65(11): 5158-5162). In another embodiment, α-ketoglutaric semialdehyde dehydrogenase (EC 1.2.1.26, for example AraE) converts adipate semialdehyde into adipate.

B. Engineered Pathways for the Production of Caprolactam

1. Caprolactam Overview

Caprolactam is primarily used in the manufacture of synthetic fibers, especially nylon 6 that is also used in bristle brushes, textile stiffeners, film coatings, synthetic leather, plastics, plasticizers, vehicles, cross linking for polyurethanes, and in the synthesis of lysine. About 2.5 billion tons of nylon 6 is produced annually on a worldwide basis. The production of nylon 6 is accomplished by the ring opening polymerization of the monomer ε-caprolactam. The starting chemical compound for the production of ε-caprolactam is benzene which is converted to either cyclohexane or phenol and either chemical is converted via cyclohexanone to cyclohexanone oxime and then this intermediate is heated in sulfuric acid. The problem to be solved therefore is to provide a synthesis route for caproic acid which not only avoids reliance on environmentally sensitive starting materials such as petroleum but also makes efficient use of non-petrochemical inexpensive, renewable resources. It would further be desirable to provide a synthesis route for caproic acid which avoids the need for significant energy inputs and which minimizes the formation of toxic by-products.

2. Engineered Pathways for the Production of Caprolactam

Aspects of the invention relates to two engineered pathways to bioproduce amino caproic acid from α-ketopimelate. The first potential pathway includes first a ketopimelate amino transferase (enzymatic step II, FIG. 2 and FIG. 3) followed by an aminopimelate decarboxylase (enzymatic step 8). Candidate genes of interest that express a ketopimelate aminotransferase activity include, but are not limited to lysN (encoding an α-aminoadipate aminotransferase from *T. thermophilus* EC 2.6.1.7) and homologs (e.g. kat2); aadat (encoding an amino adipate aminotransferase in *R. norvegicus*) and AADAT (encoding an amino adipate aminotransferase in *H. sapiens*). A list of candidate enzymes and activities was generated based on the criteria (i) demonstrated or potential conversion of 2-oxopimelate to 2-amino pimelic acid in presence of glutarate and (ii) availability of protein sequence information (see Table 3).

TABLE 3

| Desired substrate and product Candidate Enzyme | Reaction | | | |
|---|---|---|---|---|
| | 2-oxopimelate | → | 2-amino pimelic acid | |
| α-aminoadipate-aminotransferase-1 EC 2.6.1.39 Q8N5Z0 Gene: AADAT *Homosapiens* | α-aminoadipate | + 2-oxoglutarate | ⇌ | L-glutamate + α-ketoadipate |
| aminoadipate-aminotransferase EC 2.6.1.39 Q7X567 lysN *Thermus thermillus* | α-aminoadipate | + 2-oxoglutarate | ⇌ | L-glutamate + α-ketoadipate |

TABLE 3-continued

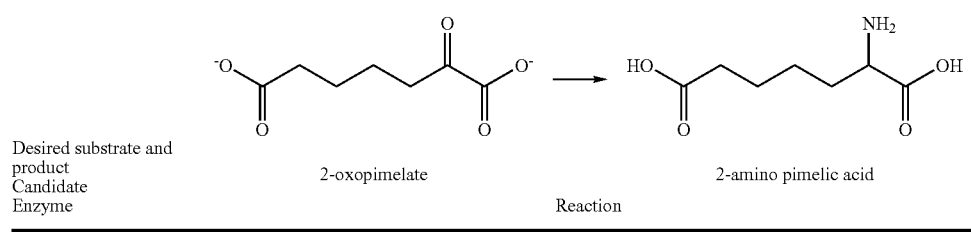

Desired substrate and product
Candidate Enzyme 2-oxopimelate → 2-amino pimelic acid Reaction diaminopimelate dehydrogenase

EC 1.4.1.16

P04964 ddb

*Corynebacterium glutamicum*

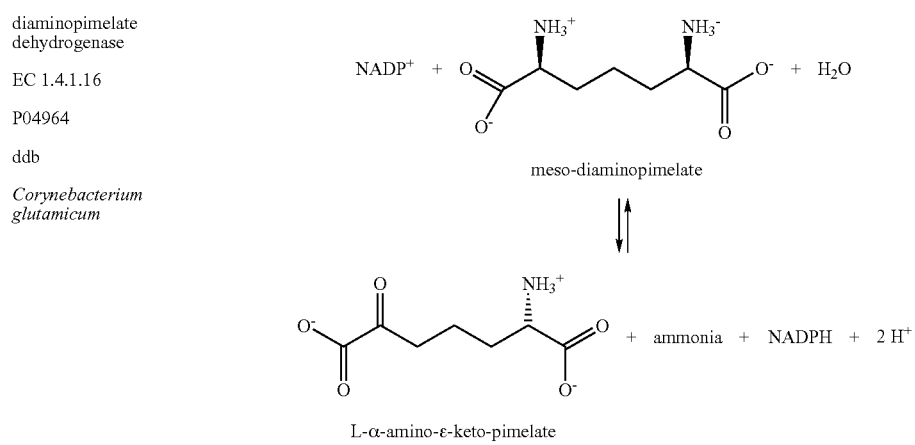

diaminopimelate dehydrogenase

EC 1.4.1.16

Q9KWR0

Dapdh

*Bacillus sphaericus*

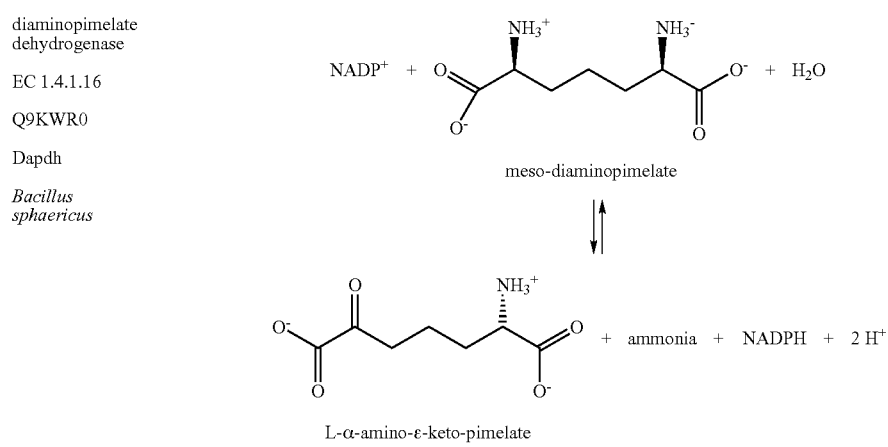

Candidate genes expressing an aminopimeleate decarboxylase activity include, but are not limited to, glutamate decarboxylases (gadA/B, encoding isoform A or isoform B in *E. coli*, GAD1 in *S. cerevisiae*, GAD1/2 in *A. thaliana*, GAD1/2 in *H. sapiens*) and their homologs. A list of candidate enzymes and activities was generated based on the criteria (i) demonstrated or potential conversion of 2-amino pimelic acid to 6-amino hexanoic acid in presence of ketoglutarate and (ii) availability of protein sequence information (see Table 4).

TABLE 4

Desired reaction / Candidate Enzyme: 2-amino pimelic acid → 6-amino hexanoic acid + $CO_2$

| Candidate Enzyme | Reaction |
|---|---|
| Glutamate decarboxylase EC 4.1.1.15 Q99259 Gad6/5 *Homo sapiens* | L-glutamate + $H^+$ ⇌ $CO_2$ + 4-aminobutyrate |
| Glutamate decarboxylase EC 4.1.1.15 Gad6/7 *Homo sapiens* | L-glutamate + $H^+$ ⇌ $CO_2$ + 4-aminobutyrate |
| Glutamate decarboxylase EC 4.1.1.15 Q07346 *Petunia hybrida* | L-glutamate + $H^+$ ⇌ $CO_2$ + 4-aminobutyrate |
| Glutamate decarboxylase EC 4.1.1.15 GadA *E. Coli* | L-glutamate + $H^+$ ⇌ $CO_2$ + 4-aminobutyrate |
| Glutamate decarboxylase EC 4.1.1.15 GadB *E. Coli* | L-glutamate + $H^+$ ⇌ $CO_2$ + 4-aminobutyrate |
| Glutamate decarboxylase EC 4.1.1.20 lysA *E. Coli* | meso-diaminopimelate + $H^+$ ⇌ $CO_2$ + L-lysine |

The second potential pathway include first a ketopimelate decarboxylase (enzymatic step 1) followed by an adipate semialdehyde aminotransferase (enzymatic step 4).

In some embodiments, the enzyme that catalyzes the decarboxylation is a KivD enzyme (as described above) or a homolog of the KivD enzyme. In some embodiments, the adipate semialdehyde aminotransferase used in the second engineered pathway includes, but is not limited the ornithine-oxo-acid transaminase (rodD from *B. subtilis*, OAT from *H. sapiens*, EC 2.6.1.13), arginine-degradative enzyme ornithine transaminase (EC 2.6.1.13), Lysine-aminotransferase (EC 2.6.1.36) from *F. lutescens* or *S. clavuligerus*, *Mus musculus* 4-aminobutyrate aminotransferase (EC 2.6.1.19), *Sus scrofa* 4-aminobutyrate aminotransferase (EC 2.6.1.19), *S. cerevisiae* 4-aminobutyrate aminotransferase (EC 2.6.1.19), *S. cerevisiae* Saccharopine dehydrogenase LYS9 and LYS1 (EC 1.5.1.10 and 1.5.1.7 respectively) or any homologous proteins from the same or other microbial species.

TABLE 5
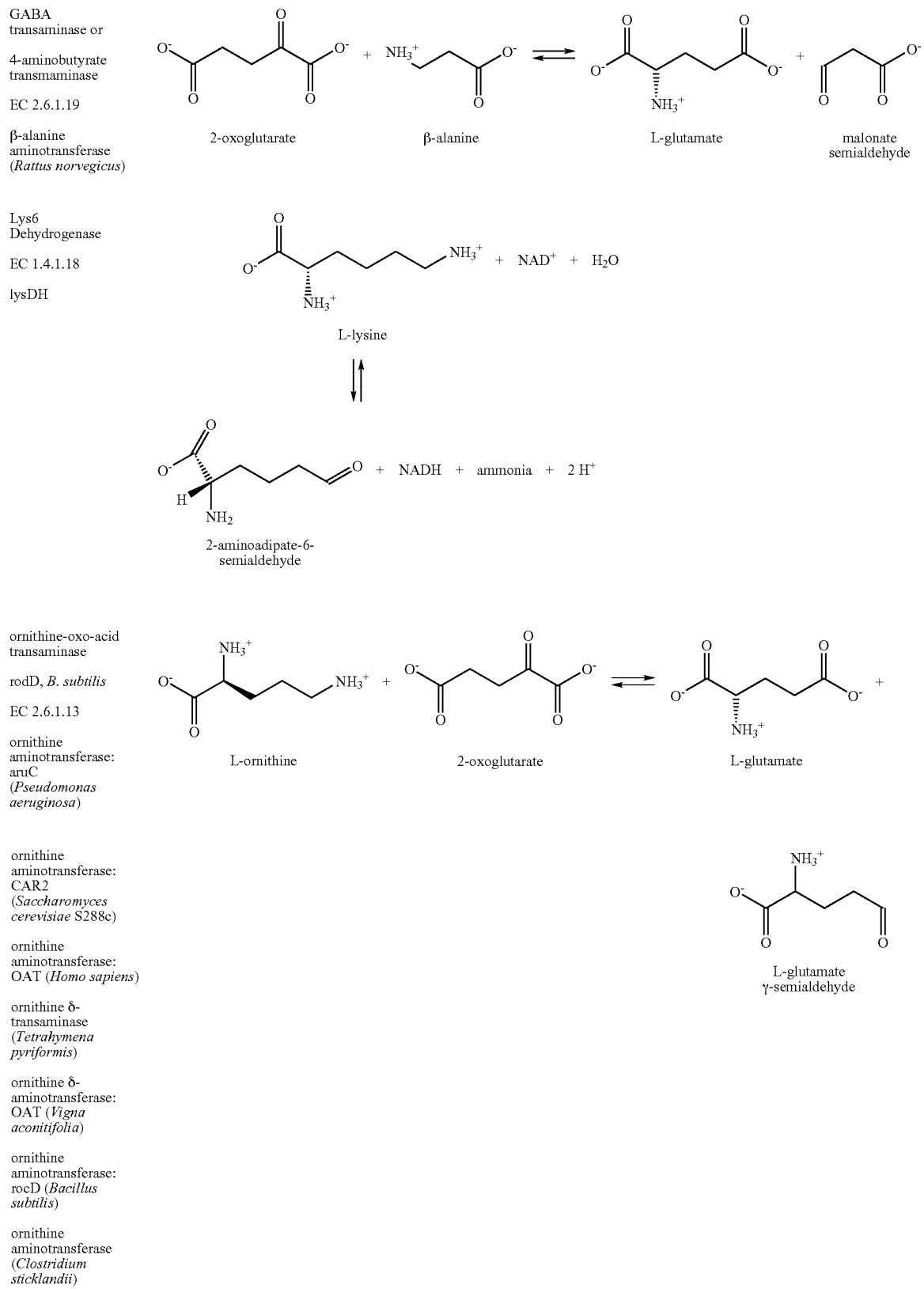

TABLE 5-continued

| Lysine-aminotransferase EC 2.6.1.36 lysine ε-aminotransferase: lat (*Strepomyces clavuligerus*) L-lysine 6-aminotransferase: lat (*Flavobacterium lutescenc*) | 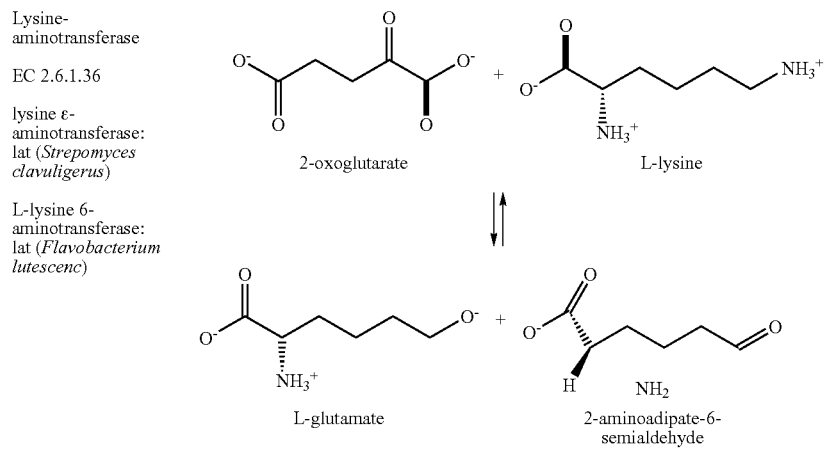 |
|---|---|

C. Engineered Pathways for the Production of Hexamethylenediamine (HMD)

Aspects of the invention relates to engineered pathways to bioproduce hexamethylene diamine from α-ketopimelate. Hexamethylene diamine is mostly used for the production of Nylon 6,6, Nylon 6,10, Nylon 6,66. Nylon 6,6 and Nylon 6,10 can be made into various kinds of nylon resins and nylon fiber.

The first engineered pathway as shown in FIGS. 2 and 3 includes first decarboxylation of 2-ketopimelate to amino caproic acid as described above in the amino caproic engineered pathway (enzymatic steps I followed by enzymatic step 4 or enzymatic step II followed by enzymatic step 8). In some embodiments, an aldehyde dehydrogenase enzyme is expressed and catalyzes the conversion of the amino caproic acid to a 6-aminohexanal intermediate (enzymatic step 5) and a 1-amintransferase enzyme is expressed and catalyzes the conversion of the 6-aminohexanal to HMD (enzymatic step 6). Alternatively, the engineered pathway comprises a phosphorylation step (using a kinase) before the dehydrogenation and the amino transfer enzymatic reactions described above. One should appreciate that the phosphorylation step and the dehydrogenation steps are analogous to the phosphorylation step (catalyzed by an aspartokinase EC 2.7.2.4) and the dehydrogenation step (catalyzed by EC 1.2.1.11 enzyme) involved in the synthesis of aspartate semialdehyde in the Lysine pathway. According to the second engineered pathway, the conversion of 2-aminopimelate produced from α-ketopimelate (enzymatic step II, FIG. 3) to hexamethylenediamine consists of enzymatic steps 9, 10 or 11, and 12 which combine enzymes or homologous enzymes characterized in the Lysine biosynthetic IV pathway. The pathway includes the following substrate to product conversions:

Enzymatic step 9: 2-aminopimelate to 2-amino-7-oxoheptanoate (or 2 aminopimelate 7 semialdehyde) as catalyzed for example by an amino adipate reductase or homolog enzyme (e.g. Sc-Lys2, EC 1.2.1.31);

Enzymatic step 10 or 11: amino-7-oxoheptanoate to 2,7-diaminoheptanoate as catalyzed for example by a saccharopine dehydrogenase (e.g. Sc-Lys9, EC 1.5.1.10 or Sc-Lys1, EC 1.5.1.7);

Enzymatic step 12: 1,7-diaminoheptanoate to hexamethylene diamine as catalyzed for example by a Lysine decarboxylase or an ornithine decarboxylase.

One should appreciate that starting from α-ketoadipate, a similar pathway will lead to the production of cadaverine.

D. Engineered Pathway for the Production of 6-Hydroxyhexanoate (6HH)

One aspect of the invention discloses an engineered pathway for the bioproduction of 6-hydroxyhaxanoate (6HH) from adipate semialdehyde, an intermediate of the adipic acid engineered pathway described above. 6HH is a 6-carbon hydroxyalkanoate that can be circularized to caprolactone or directly polymerized to make polyester plastics (polyhydroxyalkanoate PHA). In some embodiments, adipate semialdehyde is converted to 6HH by simple hydrogenation and the reaction is catalyzed by an alcohol dehydrogenase (EC 1.1.1.1). This enzyme belongs to the family of oxidoreductases, specifically those acting on the CH—OH group of donor with $NAD^+$ or $NADP^+$ as acceptor. In some embodiments, a 6-hydroxyhexanoate dehydrogenase (EC 1.1.1.258) that catalyzes the following chemical reaction is used.

6-hydroxyhexanoate+$NAD^+$ ⟷ 6-oxohexanoate+ $NADH+H^+$

Other alcohol dehydrogenases include but are not limited to adhA or adhB (from *Z. mobilis*), butanol dehydrogenase (from *Clostridium acetobutylicum*), propanediol oxidoreductase (from *E. coli*), and ADHIV alcohol dehydrogenase (from *Saccharomyces*).

E. Engineered Pathway for the Production of 1,6-Hexanediol

One aspect of the invention discloses an engineered pathway for the bioproduction of 1,6-hexanediol from adipate semialdehyde, an intermediate of the adipic acid engineered pathway described above. 1,6-hexanediol is a valuable intermediate for the chemical industry. It has applications in a variety of polymer syntheses such as the production of polyesters for polyurethane elastomers and polymeric plasticizers and is also used in gasoline refining.

In some embodiments, adipate semialdehyde is converted to 6-hydroxyhexanoate by an alcohol dehydrogenase (enzymatic step 1, FIG. 2) and then to 1,6-hexanediol by action of an alcohol dehydrogenase or an aldehyde dehydrogenase (enzymatic step 2, FIG. 2).

Alcohol dehydrogenases (ADHs) (EC 1.1.1.1 and 1.1.1.2) catalyze the reversible reduction of ketones and aldehydes to alcohols with the reduction of $NAD^+$ to NADH. In some embodiments, the alcohol dehydrogenase includes but is not limited to adhA or adhB (from *Z. mobilis*), butanol dehydrogenase (from *Clostridium acetobutylicum*), propanediol oxidoreductase (from *E. coli*), and ADHIV alcohol dehydrogenase (from *Saccharomyces*), ADH6 (from *S. cerevisiae*).

Aldehyde NAD(+) dehydrogenase activity and alcohol NAD(+) dehydrogenase activities can be carried out by two different polypeptides, or carried out by a single polypeptide, such as a multi-functional aldehyde-alcohol dehydrogenase (EC 1.2.1.10) from *E. coli* (Goodlove et al. Gene 85:209-14, 1989; GenBank Accession No. M33504). Polypeptides having aldehyde dehydrogenase (NAD(P)+) (EC 1.2.1.-) or aldehyde dehydrogenase (NAD(+)) (EC 1.2.1.3) activity as well as nucleic acid encoding such polypeptides can be obtained from various species including, without limitation, *S. cerevisiae*.

F. Engineered Pathway for the Production of 6 Aminohexanol

In some embodiments, a Cn omega-amino alcohol can be generated from a Cn terminal amino acid wherein the number of carbons is between 4 and 7, by coupling a gamma-aminobutyraldehyde dehydrogenase (EC 1.2.1.3 or 1.2.1.19 or 1.2.1.47) and an alcohol dehydrogenase. In a preferred embodiment, a 6-aminohexanol is generated from amino caproic acid by coupling a gamma-aminobutyraldehyde dehydrogenase (EC 1.2.1.3 or 1.2.1.19 or 1.2.1.47) and an aforementioned alcohol dehydrogenase with a metabolic pathway for aminocaproic acid.

IV. Engineered Pathways for the Production of Difunctional Alkanes (C5 to C8) from α-Keto Acids (C5 to C8)

Figure 5:
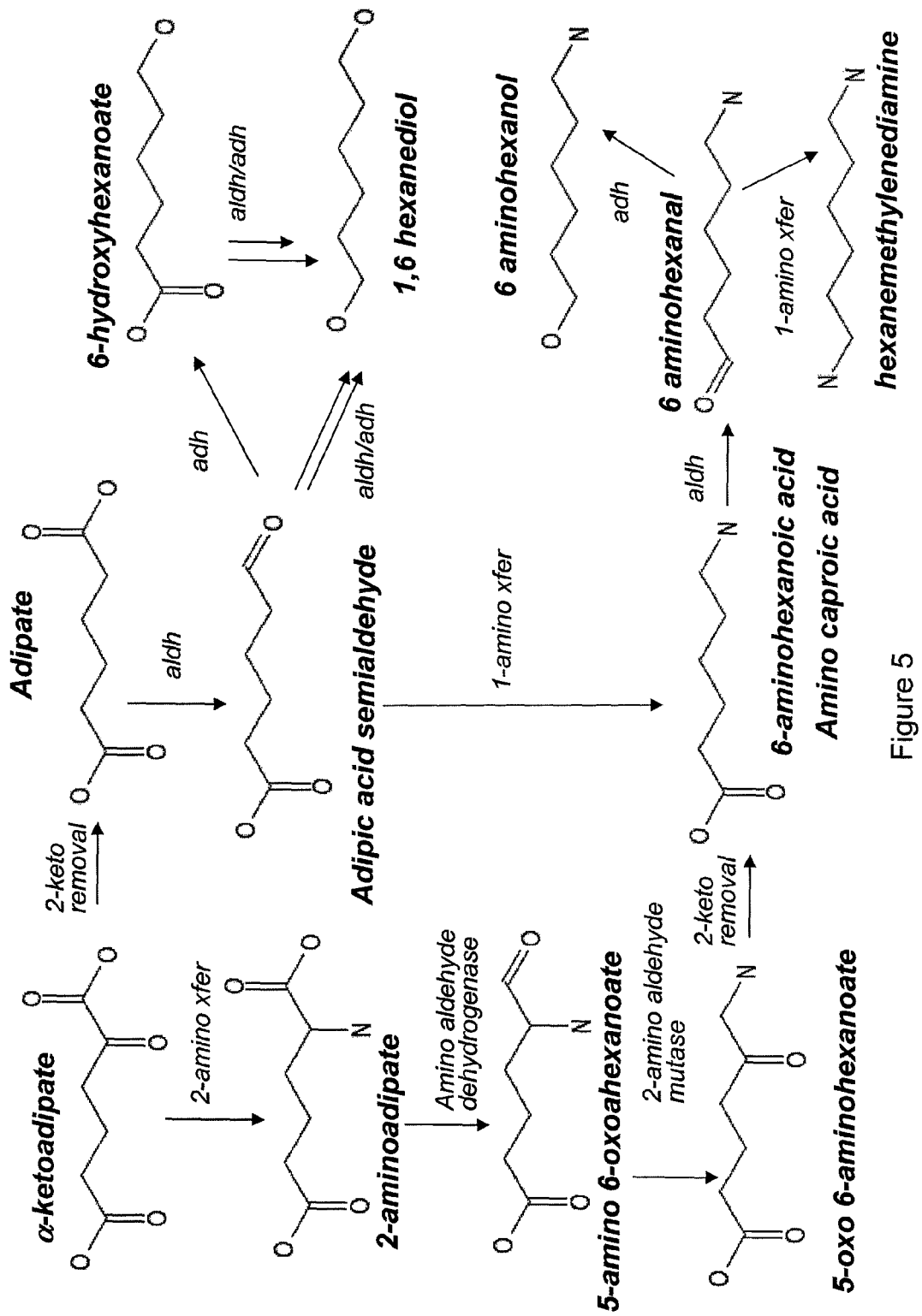
FIG. 5 represents a flow diagram for the bioproduction of difunctional hexanes Cn starting from 2-ketoadipate.

There are several potential pathways for production of difunctional alkanes (Cn) from α-keto acids (Cn) sources with recombinant microorganisms as shown in FIG. 5. Aspects of the invention relate to bioconversion of the α-keto intermediates into difunctional pentane, difunctional hexane, difunctional heptane, difunctional octane molecules. Difunctional pentane molecules of interest include, but are not limited to, 1-hydroxypentanoate, 1,5-pentanediol, glutarate, cadaverine (pentane-1,5-diamine), 5-aminopentanal and 5-aminopentanol. Difunctional hexane molecules of interest include, but are not limited to, 1-hydroxyhexanoate, 1,6-hexanediol, adipate, hexamethylenediamine, amino caproic acid, 6-aminohexanal and 6-aminohexanol. Difunctional heptane molecules of interest include but are not limited to 1-hydroxyheptanoate, 1,7-heptanediol, pimelic acid, 1,7-diaminoheptane, 7 aminoheptanal and 7-aminoheptanol. Difunctional octane molecules of interest include, but are not limited to, 1,4-octane diol, 1-hydroxyoctanoate, capylic acid, 1,4-diaminooctane, 4-aminooctanal and 4-aminooctanol.

One aspect of the invention relates to a first engineered pathway for the production of difunctional alkanes which includes a 2-aminotransferase (Enzymatic step II) as described above. According to the first engineered pathway, the conversion of α-keto acid Cn to difunctional Cn alkanes consists of enzymatic steps II, 21, 22 23 and above described steps 5, 6 and 7 including the following enzymes and substrate to product conversions:

Enzymatic step II: α-keto acid Cn to 2 amino 1,n-dicarboxylic acid as catalyzed for example by a 2-aminotransferase or homolog enzyme (e.g. lysN (EC 2.6.1.7), kat2; aadat and AADAT).

Enzymatic step 21: 2 amino 1,n-dicarboxylic acid to (n−1)-amino-n-oxocarboxylic acid as catalyzed for example by an amino aldehyde dehydrogenase.

Enzymatic step 22: (n−1)-amino-n-oxocarboxylic acid to (n−1)-oxo-n-aminocarboxylic acid as catalyzed by a 2-aminoaldehyde mutase. In an exemplary embodiment, the aminoaldehyde mutase is a glutamate-1-semialdehyde 2,1-aminomutase (EC 5.4.3.8). Glutamate-1-semialdehyde 2,1-aminomutase (GSAM) has been described in the porphyrin biosynthesis pathway and catalyzes the reaction from (S)-4-amino-5-oxopentanoate to 5-aminolevulinate.

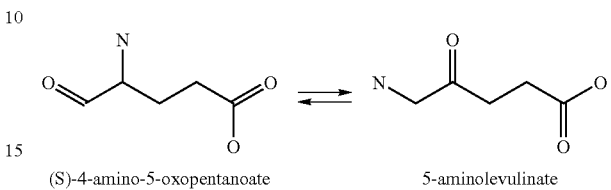

(S)-4-amino-5-oxopentanoate      5-aminolevulinate

In some embodiments, the aminoaldehyde mutase includes Glutamate-1-semialdehyde 2,1-aminomutase from thermosynechococcus elongates, from *thermus thermophilus*, and from *aeropyrum pernix* (gene hemi) and polypeptides encoded from the gsa gene form, for example, *Synechococcus* sp.

Enzymatic step 23: (n−1) oxo-n-aminocarboxylic acid to n-amino carboxylic acid as catalyzed by three enzymes: a dehydrogenase (step 23a) converting the ketone group into a secondary alcohol group. Dehydrogenation is followed by dehydratation as catalyzed by a dehydratase (step 23b) catalyzing the conversion of the secondary alcohol group to an alkene and a dehydrogenase catalyzing the conversion of the alkene into an alkane (step 23c).

Enzymatic step 5: n-amino carboxylic acid to n-amino aldehyde catalyzed by an aldehyde dehydrogenase (e.g EC 1.2.1.3) followed by either enzymatic step 6 or enzymatic step 7

Enzymatic step 6: n-amino carboxylic acid to n amino alcohol catalyzed by an alcohol dehydrogenase, for example, alcohol dehydrogenases (EC 1.1.1.1 and EC 1.1.1.2).

Enzymatic step 7: n-amino aldehyde to 1,n-diaminoalkane catalyzed by an 1-amino transferase.

Another aspect of the invention relates to a second pathway for the bioproduction of difunctional alkanes of interest (C5 to C8) from a α-keto acid of the same length (C5 to C8). The second engineered pathway includes a first α-ketone removal step (enzymatic step III). In some embodiments, the ketone removal reaction is a three steps enzymatic reactions including, a dehydrogenase catalyzing the conversion of the ketone group to a secondary alcohol; a dehydratase catalyzing the conversion of the secondary alcohol to an alkene, and a dehydrogenase catalyzing the conversion of an alkene into an alkane. In an exemplary embodiment, adipic acid is synthesized from α-ketoadipate by the conjugated activities of a first dehydrogenase, a dehydratase and second dehydrogenase. In some embodiments, the first and the second dehydrogenases are identical.

In some embodiments, the dehydrogenase is a 3-oxoacyl-[acyl-carrier protein] reductase (EC 1.1.1.100) shown to catalyze the following reaction in the fatty acid biosynthesis superpathway:

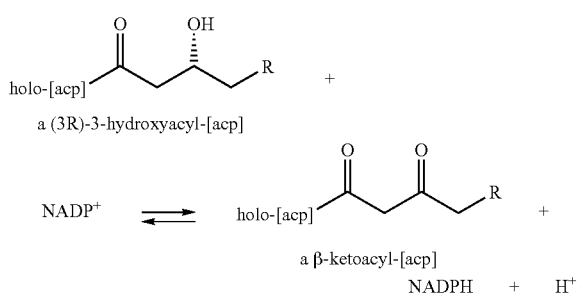

a (3R)-3-hydroxyacyl-[acp]

a β-ketoacyl-[acp]

In some embodiments, the dehydrogenase is a β-ketoacyl-[acyl-carrier-protein] reductase (FabG gene from *E. Coli*), the fatty acid synthase (Fas2 gene from *Saccharomyces cerevisiae*) or the fatty acid synthase (FASN gene from *Homo sapiens*).

In some embodiments, the dehydratase is a 3-hydroxyoctanoyl-[acyl-carrier-protein] dehydratase (EC 4.2.1.59) which catalyses the following reaction:

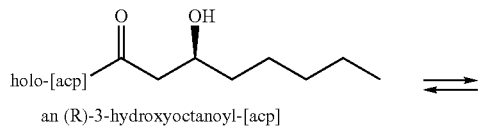

an (R)-3-hydroxyoctanoyl-[acp]

a trans oct-2-enoyl-[acp]

3-hydroxyoctanoyl-[acyl-carrier-protein] dehydratase includes, but is not limited to, 3-hydroxyacyl-ACP dehydrase from *Spinacia oleracea*, β-hydroxyacyl-ACP dehydrase (FabA gene from *E. Coli*), β-hydroxyacyl-ACP dehydratase (FabZ gene from *E. Coli*). In some embodiments, the second dehydrogenase is an enoyl acyl carrier protein reductase (EC 1.3.1.9) such as enoyl-ACP reductase (fabI gene form *E. Coli*) shown to catalyze the following reaction.

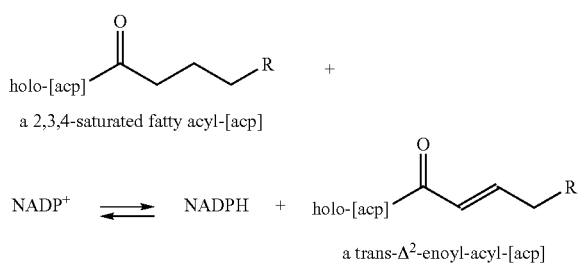

a 2,3,4-saturated fatty acyl-[acp]

a trans-Δ²-enoyl-acyl-[acp]

In some embodiments, the first and the second dehydrogenase are identical (fatty acid synthase (Fas2 gene from *Saccharomyces cerevisiae* or FASN gene from *Homo sapiens*).

Figure 4:
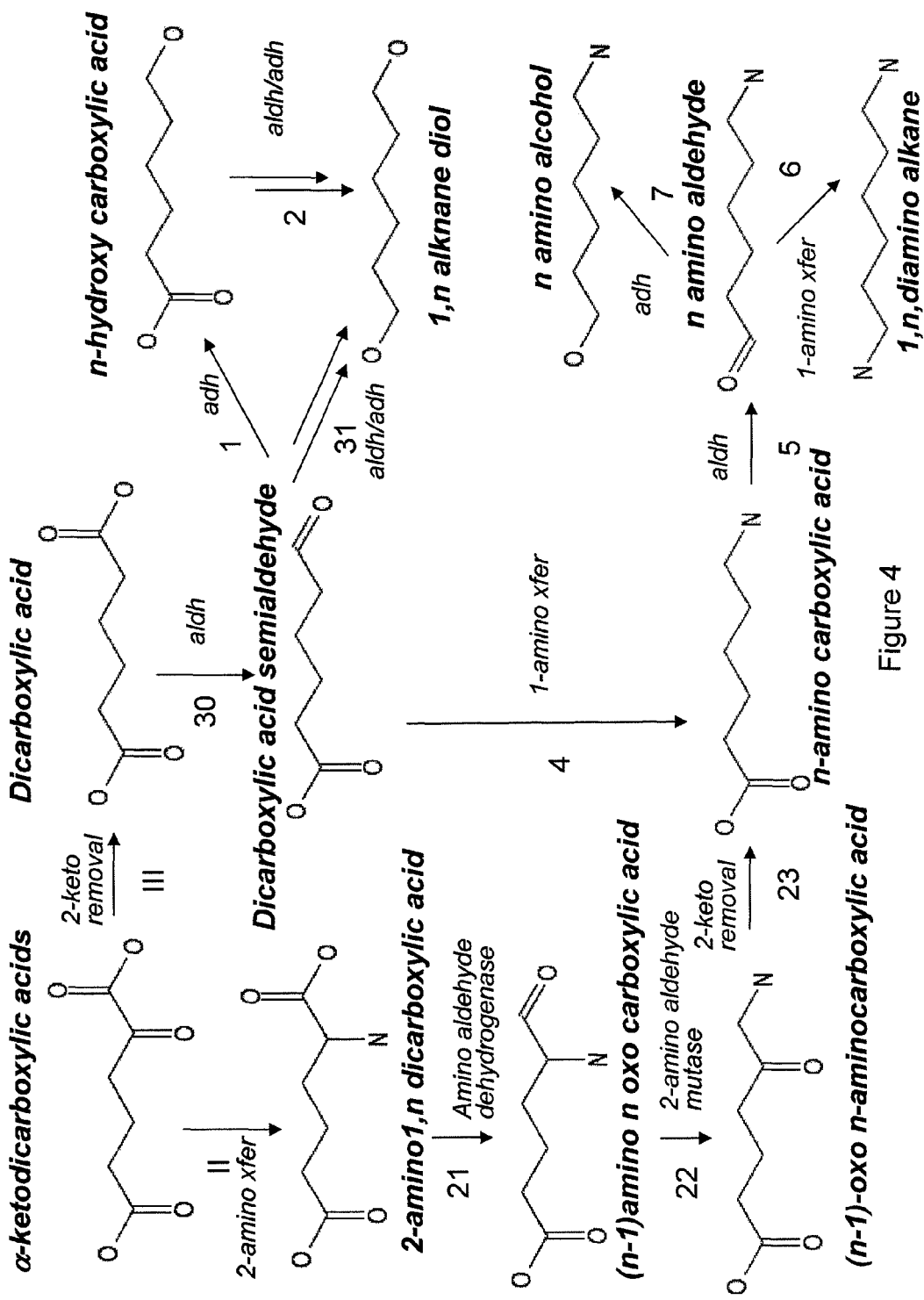
FIG. 4 represents a flow diagram for the bioproduction of difunctional alkanes Cn starting from an α-keto acid Cn.

Difunctional alkane production comprises enzymatic step 30, followed by different enzymatic steps depending on the metabolite or the final product of interest. The biological engineered pathway for the production of n-hydroxy carboxylic acid and 1,n-alkane diols includes one or more alcohol and/or aldehyde dehydrogenase. In one embodiment, the engineered pathway comprises enzymatic step 30, followed by enzymatic steps 1 and 2 or enzymatic step 30 followed by enzymatic step 31 as described below and illustrated in FIG. 4 and FIG. 5. In some embodiments, the biological engineered pathway for the production of n-amino carboxylic acid, n-amino aldehyde, n-amino alcohol or 1,n-diamino alkane comprises one or more amino transferases (enzymatic steps 4 and 6), aldehyde dehydrogenase (enzymatic step 5) and alcohol dehydrogenase (enzymatic step 7). In an exemplary embodiment, amino caproic acid is produced from 6-oxohexanoate by an engineered pathway comprising an aldehyde dehydrogenase (enzymatic step 30) followed by an aminotransferase (enzymatic step 4). Amino caproic acid can be subsequently converted to hexamethylenediamine by an aldehyde dehydrogenase (enzymatic step 5) followed by an amino transferase (enzymatic step 6). The enzymatic steps and the substrate to product conversions are listed below and illustrated in FIG. 4 and FIG. 5:

Enzymatic step 30: dicarboxylic acid to carboxylic acid semialdehyde as catalyzed by an aldehyde dehydrogenase;

Enzymatic step 1: carboxylic acid semialdehyde to hydroxyl carboxylic acid as catalyzed by an alcohol dehydrogenase;

Enzymatic step 2: hydroxycarboxylic acid to 1,n, alkane diol as catalyzed by an aldehyde dehydrogenase or an alcohol dehydrogenase.

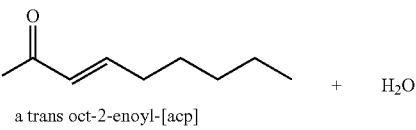

Enzymatic step 31: carboxylic acid semialdehyde to 1,n-alkane diol as catalyzed by an aldehyde dehydrogenase or an alcohol dehydrogenase.

Enzymatic step 4: carboxylic acid semialdehyde to n-amino carboxylic acid to n-amino aldehyde as catalyzed by an aldehyde dehydrogenase;

Enzymatic step 6: n-amino aldehyde to 1,n, diaminoaldehyde as catalyzed by an 1-amino transferase;

Enzymatic step 7: n-aminoaldehyde to n-amino alcohol as catalyzed by an alcohol dehydrogenase.

Screening Techniques

In accordance with the methods described herein, reaction mixtures for pathway development may be carried out in any vessel that permits cell growth and/or incubation. For example, a reaction mixture may be a bioreactor, a cell culture flask or plate, a multiwell plate (e.g., a 96, 384, 1056 well microtiter plates, etc.), a culture flask, a fermentor, or other vessel for cell growth or incubation.

Screening may be carried out by detection of expression of a selectable marker, which, in some genetic circumstances, allows cells expressing the marker to survive while other cells die (or vice versa). Efficient screening techniques are needed to provide efficient development of novel pathways using the methods described herein. Preferably, suitable screening techniques for compounds produced by the enzymatic pathways allow for a rapid and sensitive screen for the properties of interest. Visual (calorimetric) assays are optimal in this regard, and are easily applied for compounds with suitable light absorption properties. More sophisticated screening technologies include, for instance, high-throughput HPLC-MS analysis, SPME (Solid Phase Microextraction) and GC-MS (Gas chromatography-mass spectrometry) (see Handbook of analytical derivatization reaction, D. R. Knapp; John Wiley & Sons, 1979). In some instance, screening robots are connected to HPLC-MS systems for automated injection and rapid sample analysis. These techniques allow for high-throughput detection and quantification of virtually any desired compound.

Biologically produced products of interest may be isolated from the fermentation medium or cell extract using methods known in the art. For example, solids or cell debris may be removed by centrifugation or filtration. Bioproducts of interest may be isolated by distillation, liquid-liquid extraction, membrane evaporation, adsorption, or using any methods known in the art.

In some embodiments, identification of the product of interest may be performed using an HPLC. For example, the standard samples are prepared with known amounts of the organic product in the medium (e.g. adipic acid, amino caproic acid). The retention time of the adipic acid produced can then be compared to that of the authentic standard. In some embodiments, identification of the product of interest may be performed using a GC-MS. The resolved samples are then analyzed by a mass selective detector and compared to previous mass spectra and retention time of authentic standards.

In some embodiments, cellular extract may be screened for enzyme activity. For example, oxohexanoate dehydrogenase activity may be detected by measuring the rate of increase of absorbance at 340 nm as described in Donoghue and Trudgill (Eur. J. Biochem., 1975, 60:1-7).

The practice of the present methods will employ, unless otherwise indicated, conventional techniques of cell biology, cell culture, molecular biology, transgenic biology, microbiology, recombinant DNA, and immunology, engineering, robotics, optics, computer software and integration. The techniques and procedures are generally performed according to conventional methods in the art and various general references, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986); Lakowicz, J. R. Principles of Fluorescence Spectroscopy, New York: Plenum Press (1983), and Lakowicz, J. R. Emerging Applications of Fluorescence Spectroscopy to Cellular Imaging Lifetime Imaging, Metal-ligand Probes, Multi-photon Excitation and Light Quenching, Scanning Microsc. Suppl VOL. 10 (1996) pages 213-24, for fluorescent techniques, Optics Guide 5 Melles Griot® Irvine Calif. for general optical methods, Optical Waveguide Theory, Snyder & Love, published by Chapman & Hall, and Fiber Optics Devices and Systems by Peter Cheo, published by Prentice-Hall for fiber optic theory and materials.

Equivalents

The present invention provides among other things compositions and methods for metabolic engineering. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Incorporation By Reference

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

What is claimed is:

1. A metabolically engineered host cell for the production of a α,ω difunctional Cn alkane from a α-ketoacid, wherein α and ω terminal functional groups are selected from the group of —OH, —COOH and —NH3 and wherein n is an integer in the range of 4 to 8, wherein the metabolically engineered host cell is genetically modified with one or more nucleic acid sequences encoding:
    a set of at least two enzymes of a biosynthetic pathway, comprising a recombinant α-ketoacid decarboxylase capable of using the α-ketoacid as a substrate and at least a recombinant aldehyde dehydrogenase, a recombinant alcohol dehydrogenase, a recombinant aminotransferase, or a combination thereof, or
    a set of at least two enzymes of a biosynthetic pathway, comprising a recombinant 2-aminotransferase capable of using the α-ketoacid as a substrate and at least a recombinant aminodecarboxylase, a recombinant reductase, a recombinant dehydrogenase, a recombinant decarboxylase, a recombinant aldehyde dehydrogenase, a recombinant alcohol dehydrogenase, a recombinant aminotransferase, a recombinant aminoaldehyde dehydrogenase, a recombinant 2-aminoaldehyde mutase, a recombinant dehydratase or a combination thereof, or
    a set of at least two enzymes of a biosynthetic pathway, comprising a recombinant dehydrogenase capable of using the α-ketoacid as a substrate and at least a recombinant dehydratase, a recombinant aldehyde dehydrogenase, a recombinant alcohol dehydrogenase, a recombinant 1-aminotransferase, or a combination thereof.

2. The metabolically engineered host cell of claim 1, wherein the engineered host cell further comprises one or more nucleic acid sequences encoding a recombinant homocitrate synthase, a recombinant homoaconitase and a recombinant homoisocitrate dehydrogenase, or homologs thereof, for the synthesis of the α-ketoacid from α-ketoglutarate, wherein the α-ketoacid is selected from α-ketoadipate, α-ketopimelate or α-ketosuberate; and
    wherein the α,ω difunctional Cn alkane comprises amino caproic acid, adipate, hexamethylenediamine, 6 hydroxyhexamine, 1,6-hexane diol, 6-aminohexanal, 6-aminohexanol or 6-hydroxyhexanoate.

3. The metabolically engineered host cell of claim 1 for the production of adipic acid from α-ketopimelate, wherein the host cell comprises one or more nucleic acid sequences encoding a recombinant decarboxylase enzyme capable of catalyzing the conversion of α-ketopimelate to adipate semialdehyde and a recombinant aldehyde dehydrogenase enzyme capable of catalyzing the conversion of adipate semialdehyde to adipic acid.

4. The metabolically engineered host cell of claim 1 for the production of amino caproic acid from α-ketopimelate, wherein the host cell comprises one or more nucleic acid sequences encoding a recombinant aminotransferase enzyme and a recombinant decarboxylase enzyme, wherein the recombinant decarboxylase enzyme catalyzes the conversion of α-ketopimelate to adipate semialdehyde and the recombinant aminotransferase enzyme catalyzes the conversion of adipate semialdehyde to amino caproic acid.

5. The metabolically engineered host cell of claim 4 for the production of hexamethylenediamine from amino caproic acid, the host cell further comprising one or more nucleic acid sequences encoding a recombinant aldehyde dehydrogenase capable of catalyzing the conversion of amino-caproic acid to 6-aminohexanal and a recombinant amino-transferase capable of catalyzing the conversion of 6-aminohexanal to hexamethylenediamine.

6. The metabolically engineered host cell of claim 1 for the production of hexamethylenediamine from α-ketopimelate, wherein the host cell comprises one or more nucleic acid sequences encoding a recombinant aminotransferase capable of catalyzing the conversion of α-ketopimelate to 2-aminopimelate, a recombinant reductase capable of catalyzing the conversion of 2-aminopimelate to 2-amino-7-oxoheptanoate, a recombinant dehydrogenase capable of catalyzing the conversion of 2-amino-7-oxoheptanoate to 2,7 diaminoheptanoate and a recombinant decarboxylase capable of catalyzing the conversion of 2,7 diaminoheptanoate to hexamethylenediamine.

7. The metabolically engineered host cell of claim 1 for the production of 6-hydroxyhexanoate from α-ketopimelate, wherein the host cell comprises one or more nucleic acid sequences encoding a recombinant decarboxylase enzyme capable of catalyzing the conversion of α-ketopimelate to adipate semialdehyde and a recombinant alcohol dehydrogenase capable of catalyzing the conversion of 6-oxohexanoate to 6-hydroxyhexanoate.

8. The metabolically engineered host cell of claim 1 further comprising one or more nucleic acid sequences encoding at least two recombinant polypeptides selected from homocitrate synthase (EC 2.3.3.-), homoaconitase (EC 2.3.3.14), and homoisocitrate dehydrogenase (EC 1.1.1.-) capable of catalyzing the synthesis of the α-ketoacid from α-ketoglutarate, wherein the α-ketoacid is selected from the group consisting of α-ketoadipate, α-ketopimelate, α-ketosuberate or a combination thereof.

9. The metabolically engineered host cell of claim 1, wherein the host cell comprises one or more nucleic acid sequences encoding at least one recombinant polypeptide selected from a α-ketoacid decarboxylase (EC 4.1.1.-), a dehydrogenase (EC 1.1.1.-) and combination thereof, wherein the host cell produces a Cn dicarboxylic acid, a Cn hydroxycarboxylic acid or a Cn alkane diol, wherein n is an integer of the range of 4 to 7.

10. The metabolically engineered host cell of claim 1, wherein the host cell comprises one or more nucleic acid sequences encoding at least one recombinant polypeptide selected from a α-ketoacid decarboxylase (EC 4.1.1.-), an amino transferase (EC 1.4.1.-), an amino transferase (EC 2.6.1.-) and combination thereof, wherein the host cell produces a Cn aminocarboxylic acid, wherein n is an integer of the range of 4 to 7.

11. The metabolically engineered host cell of claim 10 further comprising one or more nucleic acid sequences encoding a recombinant aldehyde dehydrogenase (EC 1.2.1.3), wherein the host cell produces a Cn amino aldehyde, a Cn amino alcohol or a Cn diamino alkane, wherein n is an integer of the range of 4 to 7.

12. The metabolically engineered host cell of claim 1, wherein the host cell comprises one or more nucleic acid sequences encoding at least one recombinant polypeptide selected from a α-aminoadipate-aminotransferase (EC 2.6.1.39), a diaminopimelate dehydrogenase (EC1.4.1.16), an amino adipate reductase (EC 1.2.1.31), a saccharopine dehydrogenase (EC 1.5.1.-), a lysine decarboxylase (EC 4.1.1.18), an ornithine decarboxylase (EC4.1.1.17) and combination thereof, wherein the host cell produces a Cn diamino alkane, wherein n is an integer of the range of 4 to 7.

13. The metabolically engineered host cell of claim 1, wherein the host cell comprises one or more nucleic acid sequences encoding at least one recombinant polypeptide selected from an 3-oxoacyl-[acyl-carrier-protein] reductase (EC 1.1.1.100), a fatty acid synthase (EC 2.3.1.-), a dehydratase (EC 4.2.1.59), a 3-hydroxyoctanoyl-[acyl-carrier-protein] dehydratase (EC 4.2.1.59), an enoyl -[acyl-carrier-protein] reductase (EC 1.3.1.9) and combination thereof, wherein the host cell produces a Cn dicarboxylic acid, wherein n is an integer of the range of 5 to 8.

14. The metabolically engineered host cell of claim 13 further comprising one or more nucleic acid sequences encoding a recombinant aldehyde dehydrogenase (EC 1.2.1.3), wherein the host cell produces a Cn hydroxycarboxylic acid or a Cn alkane diol, wherein n is an integer of the range of 5 to 8.

15. The metabolically engineered host cell of claim 14 further comprising one or more nucleic acid sequences encoding at least one recombinant polypeptide selected from an amino transferase (EC 1.4.1.-) and an amino transferase (EC 2.6.1.-), wherein the host cell produces a Cn amino carboxylic acid, wherein n is an integer of the range of 5 to 8.

16. The metabolically engineered host cell of claim 15 further comprising one or more nucleic acid sequences encoding at least one recombinant polypeptide selected from an aldehyde dehydrogenase (EC 1.2.1.3), an amino transferase (EC 1.4.1.-), an amino transferase (EC 2.6.1.-) and combination thereof, wherein the host cell produces a Cn amino aldehyde, a Cn diamino alkane or a Cn amino alcohol, wherein n is an integer of the range of 5 to 8.

17. The metabolically engineered host cell of claim 1, wherein the host cell comprises one or more nucleic acid sequences encoding at least one recombinant polypeptide selected from an aminotransferase (EC 2.6.1.7), an aldehyde dehydrogenase (EC 1.2.1.3), a glutamate semialdehyde mutase (EC 5.4.3.8), an 3-oxoacyl-[acyl-carrier-protein] reductase (EC 1.1.1.100), a fatty acid synthase (EC 2.3.1. -), a dehydratase (EC 4.2.1.59), a 3-hydroxyoctanoyl -[acyl-carrier-protein] dehydratase (EC 4.2.1.59), an enoyl -[acyl-carrier-protein] reductase (EC 1.3.1.9) and combination thereof, wherein the host cell produces a Cn aminocarboxylic acid, wherein n is an integer of the range of 5 to 8.

* * * * *